US010451639B2

United States Patent
Antoni et al.

(10) Patent No.: US 10,451,639 B2
(45) Date of Patent: Oct. 22, 2019

(54) RELEASE REAGENT FOR VITAMIN D COMPOUNDS

(71) Applicant: Roche Diagnostics Operations, Inc., Indianapolis, IN (US)

(72) Inventors: Sascha Antoni, Penzberg (DE); Christian Vogl, Bichl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/243,187

(22) Filed: Aug. 22, 2016

(65) Prior Publication Data

US 2016/0356795 A1 Dec. 8, 2016

Related U.S. Application Data

(63) Continuation of application No. 14/693,985, filed on Apr. 23, 2015, now abandoned, which is a (Continued)

(30) Foreign Application Priority Data

May 20, 2010 (EP) .................................... 10163453
Mar. 15, 2011 (EP) .................................... 11158296

(51) Int. Cl.
*G01N 33/82* (2006.01)
*G01N 33/00* (2006.01)

(52) U.S. Cl.
CPC ......... *G01N 33/82* (2013.01); *G01N 2440/00* (2013.01); *Y10T 436/203332* (2015.01)

(58) Field of Classification Search
CPC ................ G01N 33/82; G01N 2440/00; Y10T 436/203332
See application file for complete search history.

(56) References Cited

U.S. PATENT DOCUMENTS

| | | | |
|---|---|---|---|
| 3,966,903 A | 6/1976 | Torii et al. | |
| 4,816,567 A | 3/1989 | Cabilly et al. | |

(Continued)

FOREIGN PATENT DOCUMENTS

| | | |
|---|---|---|
| EP | 0583945 A2 | 2/1994 |
| EP | 0753743 B1 | 1/1997 |

(Continued)

OTHER PUBLICATIONS

International Search Report dated Sep. 26, 2011 in Application No. PCT/EP2011/058048, 5 pages.

(Continued)

*Primary Examiner* — Rebecca M Fritchman
(74) *Attorney, Agent, or Firm* — Stinson LLP

(57) ABSTRACT

A reagent composition for releasing vitamin D compounds bound to vitamin D-binding protein, an in vitro method for the detection of a vitamin D compound in which the vitamin D compound is released from vitamin D-binding protein by the use of this reagent composition and the reagent mixture obtained in this manner. The use of the disclosed reagent composition to release vitamin D compounds as well as a kit for detecting a vitamin D compound which contains the reagent composition for releasing vitamin D compounds in addition to common detecting reagents.

15 Claims, 10 Drawing Sheets

Related U.S. Application Data continuation of application No. 14/501,747, filed on Sep. 30, 2014, now abandoned, which is a continuation of application No. 13/681,098, filed on Nov. 19, 2012, now abandoned, which is a continuation of application No. PCT/EP2011/058048, filed on May 18, 2011.

(56) References Cited

U.S. PATENT DOCUMENTS

| | | |
|---|---|---|
| 5,594,102 A | 1/1997 | Panzone et al. |
| 5,714,586 A | 2/1998 | Kunstmann et al. |
| 5,981,779 A | 11/1999 | Holick et al. |
| 7,087,395 B1 | 8/2006 | Garrity et al. |
| 7,482,162 B2 | 1/2009 | Laurie et al. |
| 2004/0054160 A1 | 3/2004 | Pal |
| 2004/0096900 A1 | 5/2004 | Laurie et al. |
| 2004/0132104 A1 | 7/2004 | Sackrison et al. |
| 2005/0079563 A1 | 4/2005 | Gupta |
| 2010/0068725 A1 | 3/2010 | Armbruster et al. |
| 2010/0285603 A1* | 11/2010 | Kobold ............... G01N 33/82 436/131 |

FOREIGN PATENT DOCUMENTS

| | | |
|---|---|---|
| EP | 1195373 B1 | 4/2002 |
| JP | 2009-085647 A | 4/2009 |
| JP | 5711811 B2 | 3/2015 |
| WO | 95/01960 A1 | 1/1995 |
| WO | 1999/067211 A1 | 12/1999 |
| WO | 2002/057797 A3 | 7/2002 |
| WO | 2003/023391 A2 | 3/2003 |
| WO | 2003/023394 A2 | 3/2003 |
| WO | 2004/063704 A2 | 7/2004 |
| WO | 2007/039194 A1 | 4/2007 |
| WO | 2007/140962 A3 | 12/2007 |
| WO | 2008/092917 A1 | 8/2008 |
| WO | 2011/144661 A1 | 11/2011 |

OTHER PUBLICATIONS

Bezkorovainy, Anatoly and Grohlich, Dietmar, "The Behavior of Native and Reduced-Alkylated Human Transferrin in Urea and Guanidine-HCl Solutions," Biochimica et Biophysica Acta, 1967, pp. 497-510, vol. 147.

Bouillon, R., "Clinical use of Vitamin D Metabolite Assays (Calcidiol and Calcitriol)," Calcium Regulating Hormones, Vitamin D Metabolites, and Cyclic AMP Assays and Their Clinical Application, 1990, pp. 24-47, Chapter 1.2, H. Schmidt-Gayk et al. Editors, Springer-Verlang Berlin.

Braun, Andreas et al., Interaction of the vitamin D-binding protein (group-specific component) and its ligand 25-hydroxy-vitamin D3: Binding differences of the various genetic types disclosed by isoelectric focusing, Electrophoresis, 1990, pp. 478-483, vol. 11.

Eisman, J. A. et al., "Determination of 25-Hydroxyvitamin D2 and 25-Hydroxyvitamin D3 in Human Plasma Using High-Pressure Liquid Chromatography," Analytical Biochemistry, 1977, pp. 298-305, vol. 80.

Falbe, Jürgen and Regitz, Manfred, Roempp Chemie Lexikon, 1995, pp. 26-27, 983, 987, 9th Edition, Georg Thieme Verlag, Stuttgart.

Friedmann, Theodore, "Structural Proteins of Polyoma Virus: Proteolytic Degradation of Virion Proteins by Exogenous and by Virion-Associated Proteases," Journal of Virology, Oct. 1976, pp. 520-526, vol. 20, No. 4.

Haddad, John G. and Chyu, Kyung Ja, "Competitive Protein-Binding Radioassay for 25-Hydroxycholecalciferol," Journal of Clinical Endocrinology, 1971, pp. 992-995, vol. 33.

Kawakami, Masanobu et al., Quantitative Studies of the Interaction of Cholecalciforel (Vitamin D3) and its Metabolites with Different Genetic Variants of the Serum Binding Protein for these Sterols, Biochemistry Journal, 1979, pp. 413-423, vol. 179.

Larrick, James W. and Fry, Kirk E., Recombinant antibodies, Human Antibodies and Hybridomas, 1991, pp. 172-189, vol. 2.

Londono Hernandez, Fernando Ivan et al., "Chemical Composition Evaluation and Ruminal Protein Kinetics of Some Feedstuffs Using a Gas and Ammonia Production in vitro Method," Revista Breasileira De Zootecnia, 2002, 243-255, vol. 31, No. 1.

McCafferty, John et al., Phage antibodies: filamentous phage displaying antibody variable domains, Nature, 1990, pp. 552-554, vol. 348.

Takagi, Yoshitaka and Igarashi, Shukuro, Determination of ppb Levels of Tryptophan Derivatives by Capillary Electrophoresis with Homogeneous Liquid-Liquid Extraction and Sweeping Method, Chemical and Pharmaceutical Bulletin, 2003, pp. 373-377, vol. 51, No. 4.

Van Den Ouweland, Johannes M. W. et al., "Measurement of 25-OH-vitamin D in human serum using liquid chromatography tandem-mass spectrometry with comparison to radioimmunoassay and automated immunoassay," Journal of Chromatography B, 2010, pp. 1163-1168, vol. 878.

Vogeser, Michael et al., "Candidate Reference Method for the Quantification of Circulating 25-Hydroxyvitamin D3 by Liquid Chromatography-Tandem Mass Spectrometry," Clinical Chemistry, 2004, pp. 1415-1417, vol. 50, No. 8.

Zerwekh, Joseph E., "The measurement of vitamin D: analytical aspects," Annals of Clinical Biochemistry, 2004, pp. 272-281, vol. 41.

Database Embase (Online), Accession No. EMB-0008000662, Elsevier Science Publishers, 1967, XP002645984.

\* cited by examiner

RELEASE REAGENT FOR VITAMIN D COMPOUNDS

CROSS-REFERENCE TO RELATED APPLICATIONS

This application is a continuation of U.S. application Ser. No. 14/693,985 filed Apr. 23, 2015, which is a continuation of U.S. application Ser. No. 14/501,747 filed Sep. 30, 2014, which is a continuation of U.S. application Ser. No. 13/681,098 filed Nov. 19, 2012, which is a continuation of International Application No. PCT/EP2011/058048, filed May 18, 2011, which claims the benefit of European Patent Application No. 10163453.3, filed May 20, 2010, and European Patent Application No. 11158296.1, filed Mar. 15, 2011, the disclosures of which are hereby incorporated by reference in their entirety.

BACKGROUND OF THE DISCLOSURE

An adequate supply of vitamin D is vital as the term "vitamin" already suggests. A deficiency of vitamin D leads to severe diseases such as rickets or osteoporosis. While vitamin D was still regarded as a single substance at the beginning of the last century, the vitamin D system has changed in the course of the last decades into a complex and manifold network of vitamin D metabolites. Nowadays more than 40 different vitamin D metabolic products are known (Zerwekh, J. E., Ann. Clin. Biochem. 41 (2004) 272-281).

Humans can only produce $D_3$ vitamins or calciferols by the action of ultraviolet rays from sunlight on the skin. In the blood Vitamin $D_3$ is bound to the so-called vitamin D-binding protein and transported to the liver where it is converted into 25-hydroxyvitamin $D_3$ by 25-hydroxylation. A multitude of other tissues are nowadays known to be involved in vitamin D metabolism in addition to the skin and liver, the two organs that have already been mentioned (Schmidt-Gayk, H. et al. (eds.), "Calcium regulating hormones, vitamin D metabolites and cyclic AMP", Springer Verlag, Heidelberg (1990) pp. 24-47). 25-Hydroxyvitamin D and more specifically 25-hydroxyvitamin $D_2$ and 25-hydroxyvitamin $D_3$ are the central storage form of vitamin D in the human organism with regard to their amounts. When needed these precursors can be converted in the kidneys to form the biologically active 1α,25-dihydroxyvitamin D the so-called D hormone. The biologically active vitamin D regulates among others calcium uptake from the intestine, bone mineralization and it influences a large number of other metabolic pathways such as e.g. the insulin system.

Measuring the vitamin D level itself is of little benefit when determining the vitamin D status of a patient, because concentrations of vitamin D (vitamin $D_2$ and vitamin $D_3$) fluctuate greatly depending on food uptake or exposure to sunlight. In addition vitamin D has a relatively short biological half-life in the circulation (24 hours) and it is therefore also for this reason not a suitable parameter for determining the vitamin D status of a patient. The same also applies to physiologically active forms of vitamin D (1,25-dihydroxyvitamin D). These biologically active forms also occur in relatively small and highly fluctuating concentrations (as compared to 25-hydroxyvitamin D which is disclosed and discussed in detail herein).

BRIEF SUMMARY OF THE DISCLOSURE

The present disclosure concerns a reagent composition for releasing vitamin D compounds bound to vitamin D-binding protein, an in vitro method for the detection of a vitamin D compound in which the vitamin D compound is released from vitamin D-binding protein by the use of this reagent composition and the reagent mixture obtained in this manner. It also concerns the use of the disclosed reagent composition to release vitamin D compounds as well as a kit for detecting a vitamin D compound which contains the reagent composition for releasing vitamin D compounds in addition to common detecting reagents.

An object of the present disclosure was to develop a reagent composition for release of vitamin D compounds, for example hydroxyvitamin D compounds, from vitamin D-binding protein in a sample which can at least partially overcome the problems of the prior art. A suitable reagent composition for releasing vitamin D compounds, an in vitro method for determining vitamin D compounds the use of the reagent composition and kits for the determination of vitamin D compounds using this reagent composition are described in the following and are encompassed by the attached claims.

According to an exemplary embodiment of the instant disclosure, an in vitro method for releasing a vitamin D compound from vitamin D-binding protein is provided. In some embodiments the method comprises the step of: a) providing a sample to be investigated; and b) mixing the sample from step (a) with i) a reagent containing a hydrogen carbonate salt or a substance capable of releasing hydrogen carbonate ions ($HCO_3^-$) upon hydrolysis in a concentration of 0.1 M to 2.0 M, ii) a reducing agent, and iii) an alkalinising agent, thereby releasing the vitamin D compound from vitamin D-binding protein.

According to another exemplary embodiment, a reagent composition for the release of a vitamin D compound from vitamin D-binding protein is provided comprising a substance selected from the group consisting of a hydrogen carbonate salt or a substance capable of releasing hydrogen carbonate ions ($HCO_3^-$) upon hydrolysis in a concentration of 0.1 M to 2.0 M and a reducing agent.

The present disclosure concerns an in vitro method for releasing a vitamin D compound from vitamin D-binding protein comprising the step of a) providing a sample to be investigated and b) mixing the sample from step (a) with i) a reagent containing a hydrogen carbonate salt or a substance capable of releasing hydrogen carbonate ions ($HCO_3^-$) upon hydrolysis in a concentration of 0.1 M to 2.0 M, ii) a reducing agent, and iii) an alkalinising agent, thereby releasing the vitamin D compound from vitamin D-binding protein.

In a further embodiment the present disclosure concerns an in vitro method for measuring a vitamin D compound comprising the steps of a) providing a sample to be investigated, b) mixing the sample from step (a) with i) a reagent containing a hydrogen carbonate salt or a substance capable of releasing hydrogen carbonate ions ($HCO_3^-$) upon hydrolysis in a concentration of 0.1 M to 2.0 M, ii) a reducing agent, and iii) an alkalinising agent, thereby releasing a vitamin D compound from vitamin D-binding protein, and c) measuring the vitamin D compound released in step (b).

In a further embodiment the present disclosure concerns a reagent composition for the release of a vitamin D compound from vitamin D-binding protein comprising a hydrogen carbonate salt or a substance capable of releasing hydrogen carbonate ions ($HCO_3^-$) upon hydrolysis in a concentration of 0.1 M to 2.0 M and a reducing agent.

In a further embodiment the present disclosure concerns a reagent mixture comprising a sample to be investigated, a reagent composition for the release of a vitamin D compound from vitamin D-binding protein, a hydrogen carbonate salt or a substance capable of releasing hydrogen carbonate ions ($HCO_3^-$) upon hydrolysis in a concentration of 0.1 M to 2.0 M and a reducing agent, and an alkalinising agent.

In a further embodiment the present disclosure concerns a kit for the release of a vitamin D compound from vitamin D-binding protein, which contains a reagent composition comprising a hydrogen carbonate salt or a substance capable of releasing hydrogen carbonate ions ($HCO_3^-$) upon hydrolysis in a concentration of 0.1 M to 2.0 M and a reducing agent.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

Figure 1:
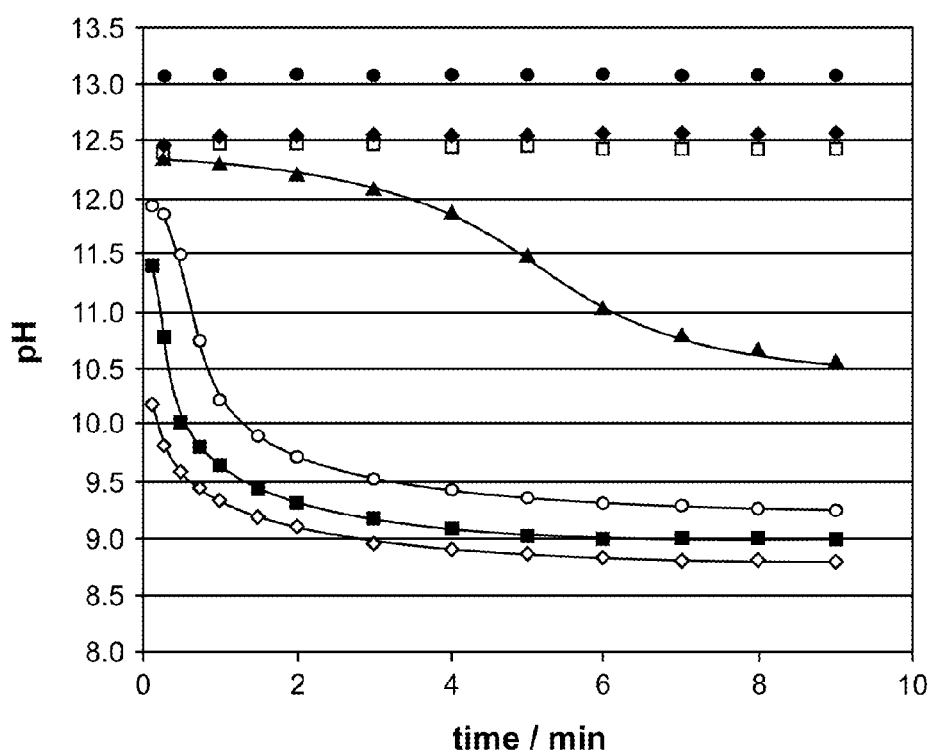
FIG. 1 pH change of the reagent mixture during the pre-treatment step. The assay was performed as outlined in example 1.5. Reagent composition (A) contains various concentrations of ethylene carbonate (EC): 0.00 M (●), 0.10 M (♦), 0.30 M (□), 0.50 M (▲), 0.75 M (○), 1.00 M (■), 1.50 M (◇) EC. The X axis shows the time in minutes, the Y axis the pH.
Figure 2:
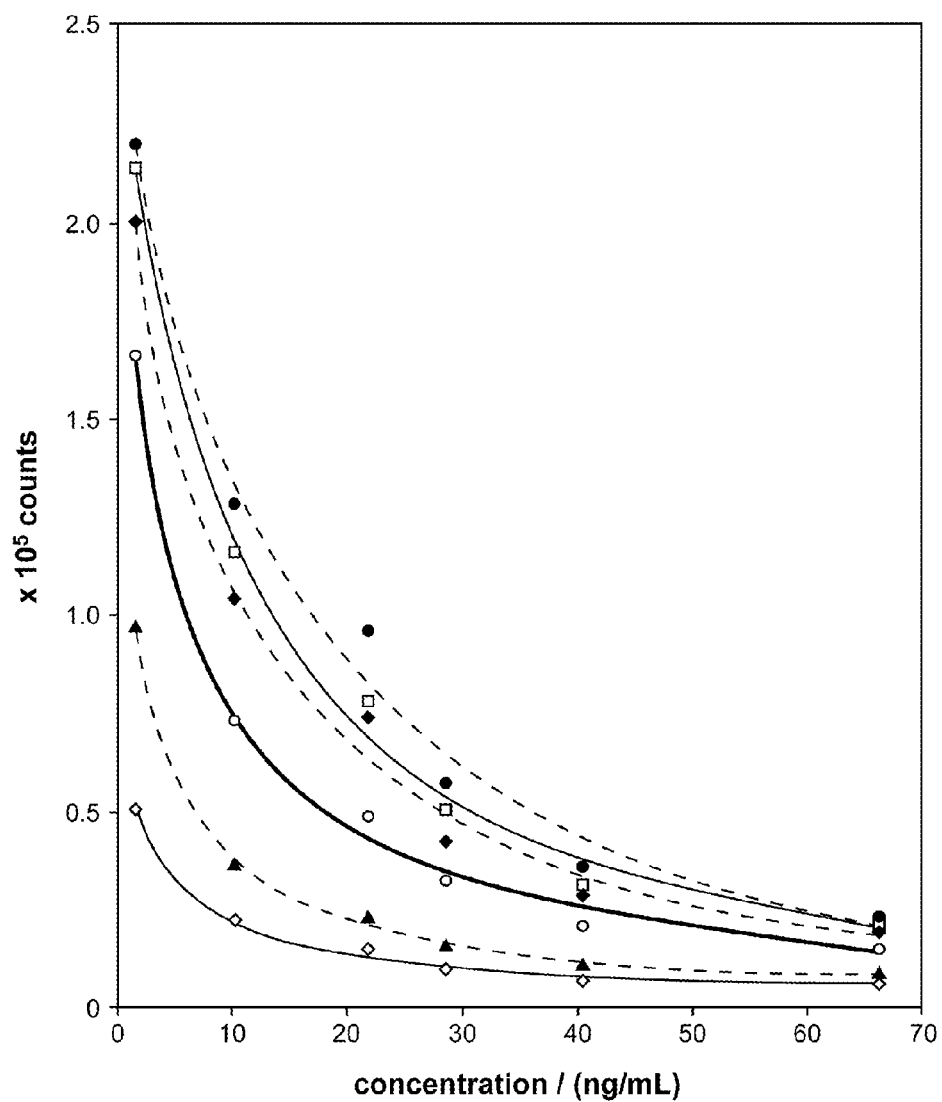
FIG. 2 Calibration curves of a Vitamin D assay as described in example 1.5 with reagent composition (A) containing various concentrations of ethylene carbonate (EC): 1.50 M (●), 1.00 M (□), 0.75 M (♦), 0.50 M (○), 0.30 M (▲) and 0.10 M (◇) EC. The X axis shows the concentration in ng/ml, the Y axis shows the counts determined as usual using the Elecsys® system from the Roche Diagnostics company.
Figure 3:
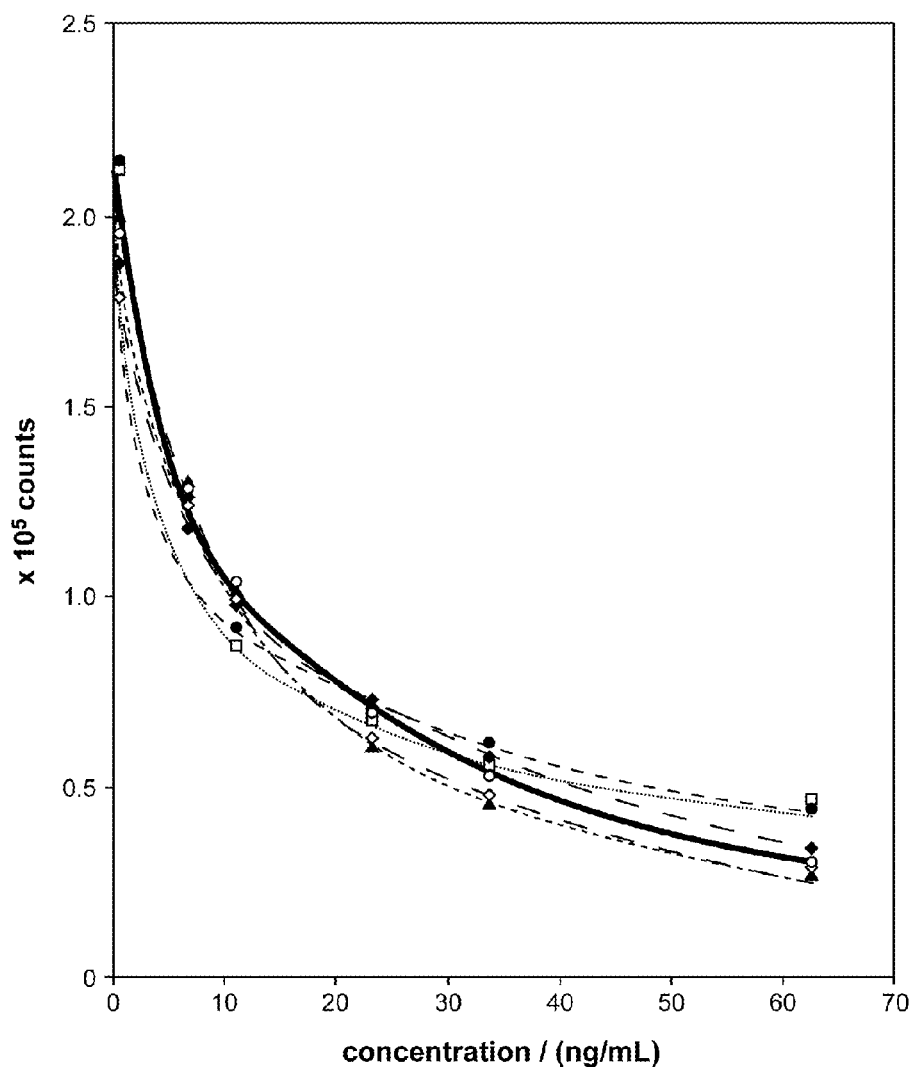
FIG. 3 Calibration curves of a Vitamin D assay as described in example 1.5 with reagent composition (A) containing various concentrations of the reducing agent dithiothreitol (DTT): 1.0 mM (□), 2.0 mM (●), 4.0 mM (♦), 6.7 mM (○), 10.0 mM/12.0 mM (▲), 15.0 mM (◇). The X axis shows the concentration in ng/ml, the Y axis shows the counts determined as usual using the Elecsys® system from the Roche Diagnostics company.
Figure 4:
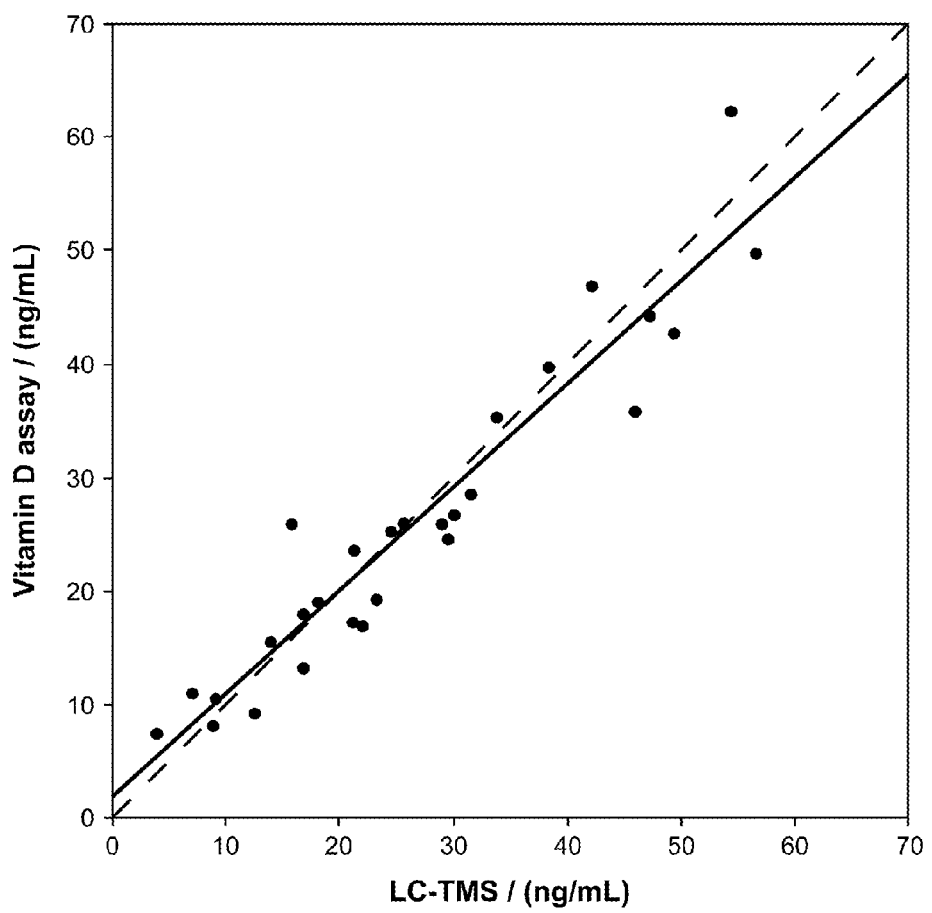
FIG. 4a Method comparison: Vitamin D assay (example 1) and liquid chromatography-tandem mass spectrometry (LC-TMS) 25-hydroxyvitamin D was determined by means of LC-TMS as well as by means of the vitamin D assay of example 1.5, where reagent composition (A) with 0.5 M ethylene carbonate (EC) was used for the incubation. The results in ng/ml for multiple serum samples are plotted on the X axis for the LC-TMS and on the Y axis for the vitamin D assay of example 1.5. ( - - - ) y=x; (—) Linear regression; Vitamin D assay=2.0116+0.9036*x, Pearsons r=0.9509.
FIG. 4b Method comparison: Vitamin D assay (example 1) and LC-TMS 25-hydroxyvitamin D was determined by means of LC-TMS as well as by means of the vitamin D assay of example 1.5, where reagent composition (A) without ethylene carbonate (EC) was used for the incubation. The results in ng/ml for multiple serum samples are plotted on the X axis for the LC-TMS and on the Y axis for the vitamin D assay of example 1.5. ( - - - ) y=x; (—) Linear regression; Vitamin D assay=0.7496+0.7338*x, Pearsons r=0.7914.
Figure 4:
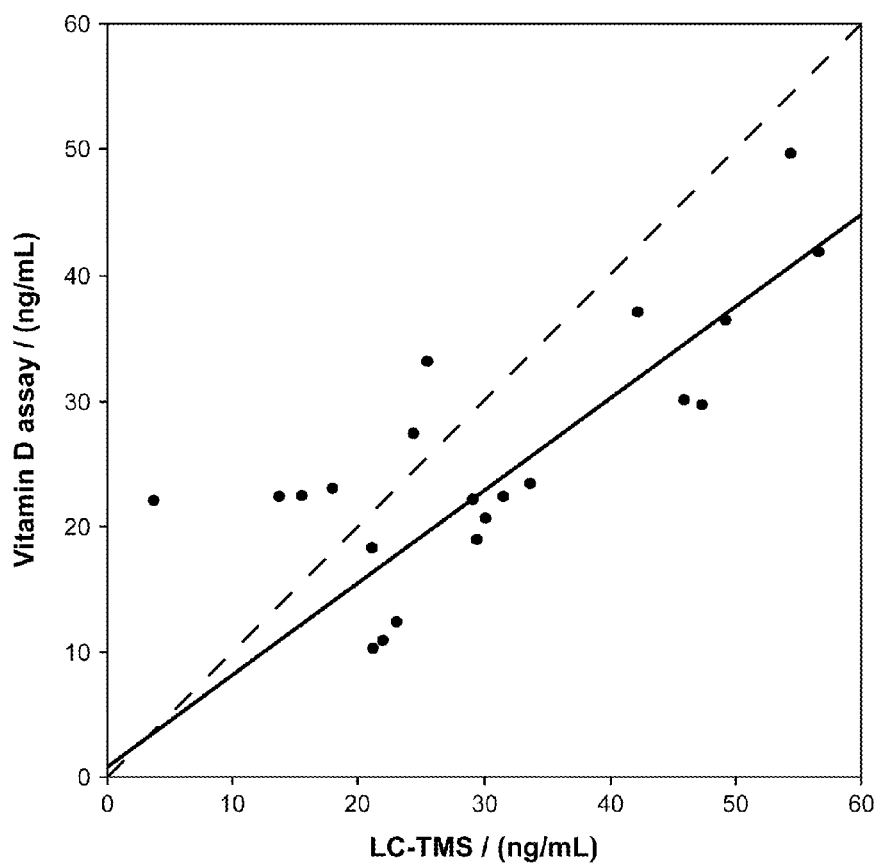

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

As noted above, measuring the vitamin D level itself is of little benefit when determining the vitamin D status of a patient, because concentrations of vitamin D (vitamin $D_2$ and vitamin $D_3$) fluctuate greatly depending on food uptake or exposure to sunlight and because vitamin D has a relatively short biological half-life. As disclosed and provided herein, however, the quantification of 25-hydroxyvitamin D provides a suitable means to globally analyse the total vitamin D status of a patient.

Vitamin D metabolites like 25-hydroxyvitamin D are bound with high affinity by vitamin D-binding protein and to a limited extend also to albumin and some lipoproteins.

Methods appropriate to release a vitamin D metabolite from vitamin D-binding protein will under normal circumstances also be more than appropriate to release a vitamin D metabolite also from any other protein.

The binding of 25-hydroxyvitamin D or other vitamin D compounds to the vitamin D-binding protein, however, complicates the determination of vitamin D compounds. All known methods require that the vitamin D compound to be analysed is released or detached from the complex that it forms with the vitamin D-binding protein. In the following this is referred to as the release of a vitamin D compound from vitamin D-binding protein for the sake of simplification although of course it can only be released from a complex of vitamin D compound and vitamin D-binding protein and not from the vitamin D-binding protein alone.

The vitamin D-binding protein is unfolded at acidic pH but has a high tendency to correctly refold and to re-bind the analyte when the pH is shifted back to neutral conditions. Hence, it is often necessary to firstly release vitamin D compounds and then to separate the vitamin D-binding protein from the vitamin D compounds to be analysed.

The present disclosure provides an in vitro method for releasing a vitamin D compound from vitamin D-binding protein comprising the step of a) providing a sample to be investigated, b) mixing the sample from step (a) with i) a reagent containing a hydrogen carbonate salt or a substance capable of releasing hydrogen carbonate ions ($HCO_3^-$) upon hydrolysis in a concentration of 0.1 M to 2.0 M, ii) a reducing agent, and iii) an alkalinising agent, thereby releasing the vitamin D compound from vitamin D-binding protein.

As used herein, each of the following terms has the meaning associated with it in this section. The articles "a" and "an" are used herein to refer to one or to more than one (i.e. to at least one) of the grammatical object of the article. The expression "one or more" denotes 1 to 50, including 1 to 20 or 2, 3, 4, 5, 6, 7, 8, 9, 10, 12, or 15. If not stated otherwise the term "vitamin D compound" is to be understood to include all naturally occurring compounds which contain the backbone of vitamin D2 or the backbone of vitamin D3 according to the following structural formulae I and II.

Formula I

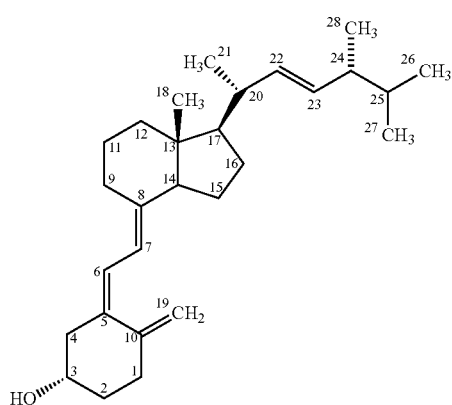

Formula II

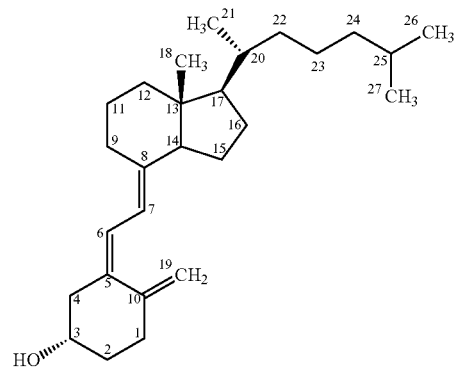

In the structural formulae I and II the positions of vitamin D are stated according to the steroid nomenclature. The 25-hydroxyvitamin D denotes vitamin D metabolites that are hydroxylated at position 25 of the structural formulae I and II i.e. the 25-hydroxyvitamin $D_2$ as well as the 25-hydroxyvitamin $D_3$. Additional known hydroxyvitamin D compounds are e.g. the 1,25-dihydroxyvitamin D and 24,25-dihydroxyvitamin D forms. 1,25-Dihydroxyvitamin D refers to the active forms of vitamin D (the so-called D hormones) that have a hydroxylation at position 1 as well as at position 25 of the structural formulae I and II. Other well known vitamin D compounds are 24,25-dihydroxyvitamin $D_2$, 24,25-dihydroxyvitamin $D_3$ and C3-epi 25-hydroxyvitamin D.

Surprisingly it has been found by the inventors, that the presence of a hydrogen carbonate salt or a substance capable of releasing hydrogen carbonate ions ($HCO_3^-$) upon hydrolysis under alkaline conditions in the in vitro method disclosed in the present disclosure leads to the release of vitamine D compounds from vitamin D-binding protein.

A "hydrogen carbonate ion" (bicarbonate ion) according to the present disclosure is an anion with the empirical formula $HCO_3^-$ and a molecular mass of 61.01 Daltons. A "hydrogen carbonate salt" according to the present disclosure is a compound selected from the group consisting of sodium hydrogen carbonate ($NaHCO_3$), potassium hydrogen carbonate ($KHCO_3$), ammonium hydrogen carbonate ($NH_4HCO_3$), calcium hydrogene carbonate ($Ca(HCO_3)_2$) and magnesium hydrogen carbonate ($Mg(HCO_3)_2$. A "substance capable of releasing hydrogen carbonate ions ($HCO_3^-$) upon hydrolysis" according to the present disclosure is a compound selected from the group consisting of carbonate esters or pyrocarbonates.

A "carbonate ester" according to the present disclosure is a carbonyl group flanked by two alkoxy groups. The general structure of these carbonates is $R_1O(C=O)OR_2$. There are cyclic carbonate esters (e.g. ethylene carbonate) or non-cyclic carbonate esters (e.g. dimethyl carbonate) as well as hydroxylated or halogenized derivatives thereof available.

According to embodiments of the instant disclosure, the hydrogen carbonate salt or a substance capable of releasing hydrogen carbonate ions ($HCO_3^-$) upon hydrolysis according to step i) of the method has a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively.

In an embodiment the present disclosure concerns an in vitro method for releasing a vitamin D compound from vitamin D-binding protein comprising the step of a) providing a sample to be investigated, b) mixing the sample from step (a) with i) a reagent containing a hydrogen carbonate salt in a concentration of 0.1 to 2.0 M, ii) a reducing agent, and iii) an alkalinising agent, thereby releasing the vitamin D compound from vitamin D-binding protein.

According to embodiments of the instant disclosure, the hydrogen carbonate salt according to step i) of the method has a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively.

According to embodiments of the instant disclosure, the hydrogen carbonate salt is selected from the group consisting of sodium hydrogen carbonate, potassium hydrogen carbonate, ammonium hydrogen carbonate, calcium hydrogen carbonate and magnesium hydrogen carbonate. According to further embodiments of the instant disclosure, the hydrogen carbonate salt is selected from the group consisting of sodium hydrogen carbonate, potassium hydrogen carbonate and ammonium hydrogen carbonate. According to even further embodiments of the instant disclosure, the hydrogen carbonate salt is selected from the group consisting of sodium hydrogen carbonate and potassium hydrogen carbonate.

In an embodiment the present disclosure concerns an in vitro method for releasing a vitamin D compound from vitamin D-binding protein comprising the step of a) providing a sample to be investigated, b) mixing the sample from step (a) with i) a reagent containing a substance capable of releasing hydrogen carbonate ions ($HCO_3^-$) upon hydrolysis in a concentration of 0.1 to 2.0 M, ii) a reducing agent, and iii) an alkalinising agent, thereby releasing the vitamin D compound from vitamin D-binding protein.

According to embodiments of the instant disclosure, the substance capable of releasing hydrogen carbonate ions ($HCO_3^-$) upon hydrolysis according to step i) of the method has a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively.

According to embodiments of the instant disclosure, the substance capable of releasing hydrogen carbonate ions ($HCO_3^-$) upon hydrolysis is a cylic or non-cyclic carbonate ester or a hydroxylated or halogenized derivative thereof, respectively. In further embodiments the substance capable of releasing hydrogen carbonate ions ($HCO_3^-$) upon hydrolysis is a cylic or non-cyclic carbonate ester or a halogenized derivative thereof, respectively. In further embodiments the cylic or non-cyclic carbonate ester or the halogenized derivative thereof is selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one, 4,5-dichloro-1,3-dioxolan-2-one, 2,5-dioxahexanedioic acid dimethyl ester, pyrocarbonate, 1,2 butylene carbonate, cis 2,3 butylene carbonate and trans 2,3 butylene carbonate. Further, the cylic or non-cyclic carbonate ester or the halogenized derivative thereof may be selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one and 4,5-dichloro-1,3-dioxolan-2-one.

According to embodiments of the instant disclosure, the cylic or non-cyclic carbonate ester is selected from the group consisting of ethylene carbonate, dimethyl carbonate, glycerol 1,2-carbonate, propylene carbonate and vinylene carbonate. According to embodiments of the instant disclosure, the cylic or non-cyclic carbonate ester is selected from the group consisting of ethylene carbonate, dimethyl carbonate, glycerol 1,2-carbonate and propylene carbonate. According to embodiments of the instant disclosure, the cylic or non-cyclic carbonate ester is selected from the group consisting of ethylene carbonate, dimethyl carbonate and glycerol 1,2-carbonate.

In an embodiment said cyclic or non-cyclic carbonate ester according to step i) of the method has a concentration of 0.1 M to 2.0 M. According to embodiments of the instant disclosure, the cyclic or non-cyclic carbonate ester has a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively.

In an embodiment the reagent containing a hydrogen carbonate salt or a substance capable of releasing hydrogen carbonate ions ($HCO_3^-$) upon hydrolysis of step (i) according to the method of the present disclosure is soluble to at least 2 M in an aqueous solution under the appropriate conditions for releasing a vitamin D compound from vitamin D-binding protein. In a further embodiment the reagent containing a hydrogen carbonate salt or a substance capable of releasing hydrogen carbonate ions ($HCO_3^-$) upon hydrolysis of step (i) according to the method of the present disclosure is soluble to at least 1.5 M, or in some embodiments is soluble to at least 1.0 M, in an aqueous solution under the appropriate conditions for releasing a vitamin D compound from vitamin D-binding protein. Hydrogen carbonate salt or a substance capable of releasing hydrogen carbonate ions ($HCO_3^-$) upon hydrolysis in water to achieve the reagent of step (i) of the method according to the present disclosure may be performed according to any known method. The hydrogen carbonate salt or the substance capable of releasing hydrogen carbonate ions ($HCO_3^-$) upon hydrolysis should be soluble in water at 25° C. The hydrogen carbonate salt or the substance capable of releasing hydrogen carbonate ions ($HCO_3^-$) upon hydrolysis solubilized in an aqueous solution should be storable at a temperature of 4° C. without drop out or crystallization.

According to the instant disclosure, the molar ratio of the hydrogen carbonate salt or the substance capable of releasing hydrogen carbonate ions ($HCO_3^-$) upon hydrolysis, respectively, to the alkalinising agent may be between 1:3 and 3:1, or between 1:2 and 2:1 and in some cases between 1:1.5 and 1.5:1.

The molar ratio of alkalinising agent to hydrogen carbonate salts and/or substances capable of releasing hydrogen carbonate ions ($HCO_3^-$) upon hydrolysis is calculated on the corresponding concentrations of the reactive ions $OH^-$ or $HCO_3^-$.

A mixture of at least two different hydrogen carbonate salts and/or different substances capable of releasing hydrogen carbonate ions ($HCO_3^-$) upon hydrolysis, respectively, can be used in a method according to the present disclosure. According to embodiments of the instant disclosure, the molar ratio of said mixtures of hydrogen carbonate salts and/or the substance capable of releasing hydrogen carbonate ions ($HCO_3^-$) upon hydrolysis to the alkalinising agent is between 1:3 and 3:1, ory between 1:2 and 2:1 or even between 1:1.5 and 1.5:1.

Without being bound by theory, it may well be that the presence of a hydrogen carbonate salt or a substance capable of releasing hydrogen carbonate ions ($HCO_3^-$) upon hydrolysis in the reagent composition induces a pH shift. Lower concentrations of said hydrogen carbonate salt or said substance capable of releasing hydrogen carbonate ions ($HCO_3^-$) upon hydrolysis in a reagent composition cause a slower pH reduction of the reagent mixture during the pre-treatment reaction. Higher concentrations of said hydrogen carbonate salt or said substance capable of releasing hydrogen carbonate ions ($HCO_3^-$) upon hydrolysis in the reagent composition cause a faster pH reduction of the reagent mixture during the pre-treatment reaction. It also would appear that due to the concerted action of a hydrogen carbonate salt or a substance capable of releasing hydrogen carbonate ions ($HCO_3^-$) upon hydrolysis and reducing agent at alkaline buffer conditions an irreversible denaturation of vitamin D-binding protein is achieved and thereby later detection of a vitamin D compound is facilitated.

In an embodiment the reducing agent of step ii) according to the method is selected from the group consisting of 2-Mercaptoethanol, 2-Mercaptoethylamine-HCl, TCEP, Cystein-HCl, Dithiothreitol (DTT), N-Methylmaleimide, Ellman's Reagent and 1,2-dithiolane-3-carboxylic acid.

In a further embodiment the reducing agent of step ii) according to the method is characterized in that the reducing agent of step ii) contains thiol goups.

In a further embodiment the reducing agent of step ii) according to the method is selected from the group consisting of 2-Mercaptoethanol, 2-Mercaptoethylamine-HCl, TCEP, Cystein-HCl and Dithiothreitol (DTT).

In an embodiment the reducing agent of step ii) according to the method has a concentration from 2 mM to 30 mM, in a further embodiment from 3 mM to 20 mM, in a further embodiment from 3.5 mM to 15 mM, and in a further embodiment from 4 mM to 10 mM.

An "alkalinising agent" can be an alkali hydroxide or alkaline earth metal hydroxide (i.e. in an aqueous solution). An alkalinising agent may also comprise a mixture of alkali hydroxides and/or alkaline earth metal hydroxides, i.e. NaOH and KOH, NaOH and LiOH, NaOH and $Ca(OH)_2$, KOH and $Ca(OH)_2$, KOH and LiOH, as well as other combinations.

"Alkali hydroxides" are a class of chemical compounds which are composed of an alkali metal cation and the hydroxide anion (OH—). Alkali hydroxides are such as NaOH, KOH, LiOH, RbOH and CsOH. "Alkali metals" are a series of chemical elements forming Group 1 (IUPAC style) of the periodic table: lithium (Li), sodium (Na), potassium (K), rubidium (Rb), caesium (Cs), and francium (Fr).

"Alkaline earth metal hydroxides" are a class of chemical compounds which are composed of an alkaline earth metal cation and 2 hydroxide anions (OH—). "Alkaline earth metals" comprising Group 2 (IUPAC style) (Group IIA) of the periodic table: beryllium (Be), magnesium (Mg), calcium (Ca), strontium (Sr), barium (Ba) and radium (Ra).

In an embodiment the alkalinising agent of step iii) according to the method of the present disclosure is selected from the group consisting of NaOH, KOH, $Ca(OH)_2$ and LiOH.

In a further embodiment the alkalinising agent of step iii) according to the method has a concentration of 0.1 M to 2.0 M, or of 0.1 M to 1.5 M, or of 0.2 M to 1.75 M or of 0.2 M to 1.0 M, or of at least 0.1, 0.2, 0.3 or 0.4 M, or of at most 2.0, 1.7, 1.5, 1.3, 1.0 or 0.75 M, respectively. In a further embodiment the alkalinising agent of step iii) according to the method is selected from the group consisting of NaOH and KOH. In a further embodiment the alkalinising agent used in the method according to the present disclosure has in the mixture of sample+reagent i)+reducing agent ii)+ alkalinising agent iii) a final concentration of 0.1 M to 0.6 M, or of 0.2 M to 0.5 M, or of at least 0.1 or 0.2 M, or of at most 0.6 or 0.5 M, respectively. In a further embodiment of the method the mixing ratio of the three reagents of steps i) ii) and iii), respectively, to a sample to be investigated may be between 1:3 and 3:1.

In an embodiment the sample of step a), the reagent of step i) containing a hydrogen carbonate salt or a substance capable of releasing hydrogen carbonate ions ($HCO_3^-$) upon hydrolysis+the reducing agent of step ii)+the alkalinising agent of step iii) according to the method might be added in any pipetting sequence. Upon mixing, step b) according to the method of the present disclosure may be in a further embodiment characterized in that it has at least for 10, 12, 15, or 20 seconds a pH value of 9.5 to 14, further step b) has upon mixing at least for 10, 12, 15, or 20 seconds a pH value of 10.5 to 14.

In an embodiment of the method the sample to be investigated of step a) is mixed in step b) with the reagent of step i) containing a hydrogen carbonate salt or a substance capable of releasing hydrogen carbonate ions ($HCO_3^-$) upon hydrolysis, the reducing agent of step ii), the alkalinising agent of step iii) and incubated. The incubation step b) can be as long as required. The incubation time is e.g. from 15 seconds to 24 h. In one embodiment the mixture of step b) according to the method of the present disclosure is incubated for 1 to 60 minutes thereby releasing vitamin D compound from vitamin D-binding protein.

The concentrations of the components of step b) according to the disclosed methods are selected such that the specified pH range and the desired concentrations of a hydrogen carbonate salt or a substance capable of releasing hydrogen carbonate ions ($HCO_3^-$) upon hydrolysis, the reducing agent and the alkalinising agent, respectively, during the incubation with the sample to be investigated are appropriate to release vitamin D compound from vitamin D-binding protein.

Alkaline conditions result in the denaturation of vitamin D-binding protein and release of vitamin D present in the sample to be investigated. The concentration of the alkalinising agent has to be sufficient to increase the pH of the "reagent mixture" (=a sample to be investigated+reagent composition according to the present disclosure+alkalinising agent) to at least pH 10.0, to at least pH 10.5, or to at least 11.0 in the pre-treatment reaction. The pH of the reagent mixture is measured at the time of mixture of the sample to be investigated+reagent composition according to the present disclosure+alkalinising agent. Due to the hydrolysis of the hydrogen carbonate salt and/or the substance capable of releasing hydrogen carbonate ions ($HCO_3^-$) upon hydrolysis, the pH will be reduced in the reagent mixture (see FIG. 1 and Example 1.5).

The term "sample" as used herein refers to a biological sample obtained from an individual for the purpose of evaluation in vitro. In the methods of the present disclosure, the sample to be investigated is in an embodiment a liquid sample. The sample may comprise in a further embodiment of the present disclosure any body fluid. In a further embodiment the sample to be investigated is blood, serum or plasma. In a further embodiment the liquid sample is dried on a filter paper or membrane. In an embodiment the sample used herein refers to an aliquot of a sample obtained from an individual.

The present disclosure in a further embodiment comprises an in vitro method for measuring a vitamin D compound comprising the steps of (a) releasing a vitamin D compound from vitamin D-binding protein and (b) measuring the vitamin D compound released in step (a).

In a further embodiment the present disclosure comprises an in vitro method for measuring vitamin D compound comprising the steps of (a) releasing a vitamin D compound bound to vitamin D-binding protein in a sample of interest and (b) measuring the vitamin D compounds released in step (a).

In a further embodiment the present disclosure concerns an in vitro method for measuring a vitamin D compound comprising the steps of a) providing a sample to be investigated, b) mixing the sample from step (a) with i) a reagent containing a hydrogen carbonate salt or a substance capable of releasing hydrogen carbonate ions ($HCO_3^-$) upon hydrolysis in a concentration of 0.1 to 2.0 M, ii) a reducing agent, and iii) an alkalinising agent, thereby releasing a vitamin D compound from vitamin D-binding protein, and c) measuring the vitamin D compound released in step (b).

In a further embodiment the present disclosure comprises an in vitro method for measuring a vitamin D compound, wherein the vitamin D compound measured is selected from the group comprising 25-hydroxyvitamin $D_2$, 25-hydroxyvitamin $D_3$, 24,25-dihydroxyvitamin $D_2$, 24,25-dihydroxyvitamin $D_3$ and C3-epi 25-hydroxyvitamin D.

In a further embodiment the present disclosure comprises an in vitro method for measuring a vitamin D compound, wherein the vitamin D compound measured is selected from the group comprising 25-hydroxyvitamin $D_2$, 25-hydroxyvitamin $D_3$, 24,25-dihydroxyvitamin $D_2$ and 24,25-dihydroxyvitamin $D_3$.

In a further embodiment the present disclosure comprises an in vitro method for measuring a vitamin D compound, wherein the vitamin D compounds 25-hydroxyvitamin $D_2$ and/or 25-hydroxyvitamin $D_3$ are determined.

Reagent Composition:

In one embodiment the present disclosure concerns a reagent composition for the release of a vitamin D compound from vitamin D-binding protein in a sample to be investigated, which contains a hydrogen carbonate salt or a substance capable of releasing hydrogen carbonate ions ($HCO_3^-$) upon hydrolysis in a concentration of 0.1 to 2.0 M and a reducing agent.

In a further embodiment the present disclosure concerns a reagent composition for the release of a vitamin D compound from vitamin D-binding protein in a sample to be investigated, which contains a hydrogen carbonate salt or a substance capable of releasing hydrogen carbonate ions ($HCO_3^-$) upon hydrolysis in a concentration of 0.1 to 1.5 M and a reducing agent.

In a further embodiment the present disclosure concerns a reagent composition for the release of a vitamin D compound from vitamin D-binding protein in a sample to be investigated, which contains a hydrogen carbonate salt or a substance capable of releasing hydrogen carbonate ions ($HCO_3^-$) upon hydrolysis in a concentration of 0.2 to 1.0 M and a reducing agent.

In a further embodiment the present disclosure concerns a reagent composition for the release of a vitamin D compound from vitamin D-binding protein in a sample to be investigated, which contains a hydrogen carbonate salt or a substance capable of releasing hydrogen carbonate ions ($HCO_3^-$) upon hydrolysis in a concentration of at least 0.1, 0.2, 0.3 or 0.4 M and a reducing agent.

In a further embodiment the present disclosure concerns a reagent composition for the release of a vitamin D compound from vitamin D-binding protein in a sample to be investigated, which contains a hydrogen carbonate salt or a substance capable of releasing hydrogen carbonate ions ($HCO_3^-$) upon hydrolysis in a concentration of at most 2.0, 1.7, 1.5, 1.3, 1.0 or 0.75 M and a reducing agent.

In a further embodiment the present disclosure concerns a reagent composition for the release of a vitamin D compound from vitamin D-binding protein in a sample to be investigated, which contains a hydrogen carbonate salt in a concentration of 0.1 M to 2.0 M and a reducing agent. According to embodiments of the instant disclosure, the reagent composition contains a hydrogen carbonate salt in a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively, and a reducing agent. According to embodiments of the instant disclosure, the hydrogen carbonate salt in the reagent composition is selected from the group consisting of sodium hydrogen carbonate, potassium hydrogen carbonate, ammonium hydrogen carbonate, calcium hydrogen carbonate and magnesium hydrogen carbonate. According to further embodiments of the instant disclosure, the hydrogen carbonate salt in the reagent composition is selected from the group consisting of sodium hydrogen carbonate, potassium hydrogen carbonate and ammonium hydrogen carbonate. In further embodiments of the instant disclosure, the hydrogen carbonate salt in the reagent composition is sodium hydrogen carbonate and/or potassium hydrogen carbonate.

In a further embodiment the present disclosure concerns a reagent composition for the release of a vitamin D compound from vitamin D-binding protein in a sample to be investigated, which contains a substance capable of releasing hydrogen carbonate ions ($HCO_3^-$) upon hydrolysis in a concentration of 0.1 M to 2.0 M and a reducing agent. According to embodiments of the instant disclosure, the reagent composition contains a substance capable of releasing hydrogen carbonate ions ($HCO_3^-$) upon hydrolysis in a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively, and a reducing agent.

In a further embodiment the present disclosure concerns a reagent composition for the release of a vitamin D compound from vitamin D-binding protein in a sample to be investigated, which contains a cylic or non-cyclic carbonate ester or a hydroxylated or halogenized derivative thereof, respectively, in a concentration of 0.1 M to 2.0 M and a reducing agent. According to embodiments of the instant disclosure, the reagent composition contains a cylic or non-cyclic carbonate ester or a halogenized derivative thereof, respectively, in a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively, and a reducing agent.

In a further embodiment the present disclosure concerns a reagent composition for the release of a vitamin D compound from vitamin D-binding protein in a sample to be investigated, which contains a cylic or non-cyclic carbonate ester or halogenized derivative thereof, respectively, in a concentration of 0.1 M to 2.0 M and a reducing agent. According to embodiments of the instant disclosure, the reagent composition contains a cylic or non-cyclic carbonate ester or halogenized derivative thereof, respectively, in a concentration of 0.1 M to 1.5 M, or of 0.2 M to 1.0 M, or of at least 0.1, 0.2, 0.3 or 0.4 M, or of at most 2.0, 1.7, 1.5, 1.3, 1.0 or 0.75 M, respectively, and a reducing agent. In further embodiments the cylic or non-cyclic carbonate ester or the halogenized derivative thereof in the reagent composition is selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one, 4,5-dichloro-1,3-dioxolan-2-one, 2,5-dioxahexanedioic acid dimethyl ester, pyrocarbonate, 1,2 butylene carbonate, cis 2,3 butylene carbonate and trans 2,3 butylene carbonate. Further the cylic or non-cyclic carbonate ester or the halogenized derivative thereof in the reagent composition may be selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one and 4,5-dichloro-1,3-dioxolan-2-one. Further the cylic or non-cyclic carbonate ester in the reagent composition may be selected from the group consisting of ethylene carbonate, dimethyl carbonate, glycerol 1,2-carbonate, propylene carbonate, vinylene carbonate according to some embodiments. According to embodiments of the instant disclosure, the cylic or non-cyclic carbonate ester in the reagent composition is selected from the group consisting of ethylene carbonate, dimethyl carbonate, glycerol 1,2-carbonate and propylene carbonate. According to further embodiments of the instant disclosure, the cylic or non-cyclic carbonate ester in the reagent composition is selected from the group consisting of ethylene carbonate, dimethyl carbonate and glycerol 1,2-carbonate.

The present disclosure concerns in a further embodiment a reagent composition characterized in that the reducing agent is selected from the group consisting of 2-Mercaptoethanol, 2-Mercaptoethylamine-HCl, TCEP, Cystein-HCl, Dithiothreitol (DTT), N-Methylmaleimide, Ellman's Reagent and 1,2-dithiolane-3-carboxylic acid.

In a further embodiment the present disclosure concerns a reagent composition characterized in that the reducing agent contains thiol groups.

In a further embodiment the present disclosure concerns a reagent composition characterized in that the reducing agent is selected from the group consisting of 2-Mercaptoethanol, 2-Mercaptoethylamine-HCl, TCEP, Cystein-HCl and Dithiothreitol (DTT).

The concentration of a reducing agent in a certain embodiment of the present disclosure is from 2 mM to 30 mM, in a further embodiment from 3 mM to 20 mM, in a further embodiment from 3.5 mM to 15 mM and in a further embodiment from 4 mM to 10 mM.

The capability of a reducing agent is dependent on the presence of functional, i.e., reducing groups. Therefore select the appropriate concentration of a reducing agent is selected taking into account it's number of active reducing groups.

The gene coding for the vitamin D-binding protein occurs in the human population in the form of different alleles. It is known that the polypeptides coded by these alleles differ biochemically i.e. they lead to different phenotypes. These biochemical differences also influence the binding and release of vitamin D compounds. The reagent composition according to the disclosure is suitable for releasing vitamin D compounds independently of the phenotype of the vitamin D-binding protein. An embodiment of the present disclosure is the use of a reagent composition according to the disclosure to release vitamin D compounds from vitamin D-binding protein.

The reagent composition according to the disclosure in one embodiment is used to release vitamin D compounds from vitamin D-binding protein in samples to be investigated irrespective and independent of the phenotypes of vitamin D-binding protein.

For the purpose of releasing vitamin D compounds from vitamin D-binding protein, the reagent composition according to the disclosure is mixed with a sample to be investigated, e.g. serum or plasma, and an alkalinising agent.

Reagent Mixture:

The term "reagent mixture" as used herein below comprises a sample to be investigated, a reagent composition according to the present disclosure, and an alkalinising agent.

In a further embodiment the reagent mixture is characterized in that the alkalinising agent is selected from the group consisting of NaOH, KOH, Ca(OH)$_2$ and LiOH.

In a further embodiment the reagent mixture is characterized in that the used alkalinising agent has a concentration of 0.1 M to 2.0 M, or of 0.1 M to 1.5 M, or of 0.2 M to 1.75 M, or of 0.2 M to 1.0 M, or of at least 0.1, 0.2, 0.3 or 0.4 M, or of at most 2.0, 1.7, 1.5, 1.3, 1.0 or 0.75 M, respectively.

In a further embodiment the reagent mixture is characterized in that the alkalinising agent is selected from the group consisting of NaOH and KOH.

In a further embodiment the alkalinising agent used in the method according to the present disclosure has in the reagent mixture a final concentration of 0.1 M to 0.6 M, or of 0.2 M to 0.5 M, or of at least 0.1, or 0.2 M, or of at most 0.6, or 0.5 M, respectively.

The mixing ratio of reagent composition and alkalinising agent to a sample to be investigated, according to embodiments of the instant disclosure includes between 1:3 and 3:1.

A sample to be investigated, the reagent composition disclosed and an alkalinising agent might be added in any pipetting sequence to form the reagent mixture. Upon mixing, the reagent mixture is in a further embodiment characterized in that it has at least for 10, 12, 15, or 20 seconds a pH value of 9.5 to 14. In some embodiments, the reagent mixture has upon mixing at least for 10, 12, 15, or 20 seconds a pH value of 10.5 to 14.

The sample to be investigated is mixed with the reagent composition according to the disclosure and an alkalinising agent and incubated. This step may also be called pre-treatment step. The pre-treatment step can be performed as long as required. The incubation time is e.g. for 15 seconds to 24 h. The reagent mixture in one embodiment is incubated for 1 to 60 minutes to release vitamin D compounds from vitamin D-binding protein. The reagent mixture in another embodiment is incubated for 4 to 10 minutes to release vitamin D compounds from vitamin D-binding protein.

The reagent mixture and concentrations of the components in it are selected such that the specified pH range and the desired concentrations of a hydrogen carbonate salt or a substance capable of releasing hydrogen carbonate ions ($HCO_3^-$) upon hydrolysis, the reducing agent and the alkalinising agent, respectively, during the incubation with a sample to be investigated are appropriate to release vitamin D compounds from vitamin D-binding protein.

The reagent mixture comprises in an embodiment also the substances of a hydrogen carbonate salt or a substance capable of releasing hydrogen carbonate ions ($HCO_3^-$) upon hydrolysis as described for the reagent composition of the present disclosure.

The detection of a vitamin D compound may be carried out such that at least one vitamin D compound selected from the group comprising 25-hydroxyvitamin $D_2$, 25-hydroxyvitamin $D_3$, 24,25 dihydroxyvitamin $D_2$, 24,25-dihydroxyvitamin $D_3$ and C3-epi 25-hydroxyvitamin D is detected.

In the specific detection of a vitamin D compound further incubation steps follow after the pre-treatment step. The leftover of the reducing agent present in the reagent mixture can be blocked by addition of unspecific proteins, such as e.g. human serum albumin (HSA). These unspecific proteins can be added separately or can be simply included in the solution also comprising the detecting reagent. By blocking the residual reducing capability of the reducing agent, a noncompromised detection of a vitamin D compound using a proteinaceous specific binding agent to a vitamin D compound is possible.

The solution comprising the specific binding agent will contain a pH buffer system which ensures after addition of the solution containing the specific binding agent to the reagent mixture the pH is a prerequisite for binding of a vitamin D compound to the specific binding agent. Neither the necessarily required buffer system nor the final pH are critical as long as binding of the specific binding agent to a vitamin D compound takes place. In case that vitamin D-binding protein is used as a specific binding agent, the pH during this incubation step is is selected between pH 6.0 and pH 9.0. In case that an antibody is used as a specific binding agent for a vitamin D compound, the pH during this incubation step may be between pH 5.5 and pH 7.5.

According to embodiments of the instant disclosure, the solution comprising the specific binding agent may contain a buffer system that is 20 mM to 400 mM. Also, the buffer has a molarity of between 50 mM and 350 mM or between 100 mM and 300 mM.

The in vitro method for the detection of a vitamin D compound can—based on the disclosure of the present disclosure—be carried out in various ways.

In principle all proteinaceous binding partners such as specifically binding polypeptides that bind to one or more vitamin D compound can be used as a specific binding agent. A specific binding agent can be either an antibody or vitamin D-binding protein itself.

Many commercial test systems are based on the use of solid phases coated with avidin or streptavidin (SA), for example SA-coated microtitre plates or SA-coated latices.

A biotinylated analyte derivative is for example bound to this SA solid phase before or during the test procedure. When detecting vitamin D compound this biotinylated analyte derivative compound can for example be a biotinylated 25-hydroxyvitamin $D_2$ and/or a biotinylated 25-hydroxyvitamin $D_3$.

In one embodiment of the present disclosure the in vitro method of detection is carried out as a competitive assay. In such a competitive test a derivative of vitamin D compound added in a defined amount to the test competes with the corresponding vitamin D compound from the sample for the binding sites of the specific binding agent.

The more vitamin D compound is present in the sample, the smaller is the detection signal. In one embodiment the derivative of a vitamin D compound is a biotinylated vitamin D compound. In a further embodiment the biotinylated vitamin D compound is a biotinylated 25-hydroxyvitamin $D_2$ and/or biotinylated 25-hydroxyvitamin $D_3$. In a further embodiment the biotinylated vitamin D compound is a biotinylated 25-hydroxyvitamin $D_2$.

As mentioned above, according to some embodiments of the instant disclosure, the specific binding agents for use in a detection method as disclosed in the present description are antibodies and vitamin D-binding protein. Vitamin D-binding protein, if used in a competitive assay format, will lead to an integrated measurement of all vitamin D compounds competing with its binding to one or more (biotinylated) vitamin D compound derivative. In one embodiment the vitamin D-binding protein will be detectable labelled, e.g. ruthenylated.

Use:

In one embodiment the present disclosure relates to the use of a reagent composition together with an alkalinising agent to release a vitamin D compound from vitamin D-binding protein.

In a further embodiment the present disclosure relates to the use of a reagent composition together with an alkalinising agent to release a vitamin D compound expected to be present in a sample to be investigated from vitamin D-binding protein.

In a further embodiment the present disclosure relates to the use of a reagent composition together with an alkalinising agent to release a vitamin D compound in method of detecting a vitamin D compound.

In a further embodiment the present disclosure relates to the use of a reagent composition containing 0.1 M to 2.0 M of a hydrogen carbonate salt or a substance capable of releasing hydrogen carbonate ions ($HCO_3^-$) upon hydrolysis, 2 mM to 30 mM of a reducing agent, together with a solution of 1 M to 1.5 M of an alkalinising agent to release a vitamin D compound expected to be present in a sample to be investigated from vitamin D-binding protein in method of detecting a vitamin D compound.

The use of the reagent composition comprises in an embodiment also substances of a hydrogen carbonate salt or a substance capable of releasing hydrogen carbonate ions ($HCO_3^-$) upon hydrolysis as described for the reagent composition of the present disclosure.

Kit:

In one embodiment the present disclosure relates to a kit for the release of a vitamin D compound from vitamin D-binding protein, which contains a reagent composition comprising a hydrogen carbonate salt or a substance capable of releasing hydrogen carbonate ions ($HCO_3^-$) upon hydrolysis in a concentration of 0.1 M to 2.0 M and a reducing agent.

In one embodiment the present disclosure relates to a kit for the detection of a vitamin D compound from vitamin D-binding protein, characterized in that it comprises a reagent composition which has 0.1 M to 2.0 M of a hydrogen carbonate salt or of a substance capable of releasing hydrogen carbonate ions ($HCO_3^-$) upon hydrolysis, a reducing agent, and an alkalinising agent.

In a further embodiment the present disclosure relates to a kit for the detection of a vitamin D compound from vitamin D-binding protein, characterized in that it comprises a reagent composition which has 0.1 M to 2.0 M of a hydrogen carbonate salt or of a substance capable of releasing hydrogen carbonate ions ($HCO_3^-$) upon hydrolysis, 2 mM to 30 mM of a reducing agent, and an alkalinising agent.

In a further embodiment the present disclosure relates to a kit for the detection of a vitamin D compound from vitamin D-binding protein, characterized in that it comprises a reagent composition which has 0.1 M to 2.0 M of a hydrogen carbonate salt or of a substance capable of releasing hydrogen carbonate ions ($HCO_3^-$) upon hydrolysis, 2 mM to 30 mM of a reducing agent, a solution of 1 M to 1.5 M of an alkalinising agent, in addition to the detecting components.

In a further embodiment the present disclosure relates to a kit for the detection of a vitamin D compound characterized in that it comprises a reagent composition which has a hydrogen carbonate salt or a substance capable of releasing hydrogen carbonate ions ($HCO_3^-$) upon hydrolysis, a reducing agent, a solution of an alkalinising agent, in addition to a solution comprising a specific binding agent.

In a further embodiment the present disclosure relates to a kit for the detection of a vitamin D compound characterized in that it comprises a reagent composition which has 0.1 M to 2.0 M of a hydrogen carbonate salt or of a substance capable of releasing hydrogen carbonate ions ($HCO_3^-$) upon hydrolysis, 2 mM to 30 mM of a reducing agent, a solution of 1 M to 1.5 M of an alkalinising agent and a solution comprising a specific binding agent.

In a further embodiment the present disclosure relates to a kit for the detection of a vitamin D compound characterized in that it comprises a reagent composition which has 0.1 M to 2.0 M of a hydrogen carbonate salt or of a substance capable of releasing hydrogen carbonate ions ($HCO_3^-$) upon hydrolysis, 2 mM to 30 mM of a reducing agent selected from the group consisting of 2-Mercaptoethanol, 2-Mercaptoethylamine-HCl, TCEP, Cystein-HCl and Dithiothreitol (DTT), a solution of 1 M to 1.5 M of an alkalinising agent selected from the group consisting of NaOH, KOH, $Ca(OH)_2$ and LiOH and a solution comprising a specific binding agent.

The kit comprises in an embodiment also substances of a hydrogen carbonate salt or a substance capable of releasing hydrogen carbonate ions ($HCO_3^-$) upon hydrolysis as described for the reagent composition of the present disclosure.

The reagent composition according to the disclosure has proven to be suitable for use in an automated test for vitamin D compounds. The present disclosure concerns the use of a reagent composition according to the disclosure for releasing vitamin D compounds from vitamin D-binding protein especially in a test for the determination of vitamin D compounds.

The test for a vitamin D compound may be completely automated. Completely automated in this case means that the experimenter only has to place a sample to be investigated and a reagent pack containing all components for measuring a vitamin D compound on an automated analyzer and all further steps are carried out automatically by the analyzer. By way of example, a completely automated test may be carried out on an Elecsys® analyzer from Roche Diagnostics.

The reagent composition according to the disclosure in a further embodiment is used in an in vitro method for the detection of a vitamin D compound selected from the group comprising 25-hydroxyvitamin $D_2$, 25-hydroxyvitamin $D_3$, 24,25 dihydroxyvitamin $D_2$, 24,25-dihydroxyvitamin $D_3$ and C3-epi 25-hydroxyvitamin D.

As already mentioned above 25-hydroxyvitamin $D_2$ and 25-hydroxyvitamin $D_3$ are forms of vitamin D relevant for diagnostics. In the in vitro method according to the disclosure the specific detection of 25-hydroxyvitamin $D_2$ or 25-hydroxyvitamin $D_3$ or both via a specific antibody to 25-hydroxyvitamin $D_2$ or 25-hydroxyvitamin $D_3$ also represents an exemplary embodiment.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An in vitro method for releasing a vitamin D compound from vitamin D-binding protein comprising the step of:
    a) providing a sample to be investigated and
    b) mixing the sample from step (a) with
        i) a reagent containing a hydrogen carbonate salt or a substance capable of releasing hydrogen carbonate ions ($HCO_3^-$) upon hydrolysis in a concentration of 0.1 M to 2.0 M,
        ii) a reducing agent, and
        iii) an alkalinising agent,
    thereby releasing the vitamin D compound from vitamin D-binding protein.
2. The method according to 1, wherein the reagent according to step (i) is soluble in an aqueous solution under the appropriate conditions for releasing a vitamin D compound from vitamin D-binding protein.
3. The method according to any one of 1 to 2, wherein the reagent according to step (i) contains a hydrogen carbonate salt in a concentration of 0.1 M to 2.0 M.
4. The method according to any one of 1 to 2, wherein the reagent according to step (i) contains a substance capable of releasing hydrogen carbonate ions ($HCO_3^-$) upon hydrolysis in a concentration of 0.1 M to 2.0 M.
5. The method according to any one of 1, 2 and 4, wherein the substance capable of releasing hydrogen carbonate ions ($HCO_3^-$) upon hydrolysis is a cylic or non-cyclic carbonate ester or a hydroxylated or halogenized derivative thereof, respectively.
6. The method according to any one of 1 to 5, wherein the sample is a liquid sample.
7. The method according to any one of 1 to 5, wherein the sample is blood, serum or plasma.
8. An in vitro method for measuring a vitamin D compound comprising the steps of:
    a) releasing a vitamin D compound from vitamin D-binding protein according to the method of any one of 1 to 7 and
    b) measuring the vitamin D compound released in step (a).
9. The method according to 8, wherein the vitamin D compound is selected from the group consisting of 25-hydroxyvitamin $D_2$, 25-hydroxyvitamin $D_3$, 24,25-dihydroxyvitamin $D_2$, 24,25-dihydroxyvitamin $D_3$ and C3-epi 25-hydroxyvitamin D.
10. The method according to 9, wherein the vitamin D compounds 25-hydroxyvitamin $D_2$ and/or 25-hydroxyvitamin $D_3$ are determined.
11. A reagent composition for the release of a vitamin D compound from vitamin D-binding protein comprising a substance selected from the group consisting of a hydrogen carbonate salt or a substance capable of releasing hydrogen carbonate ions ($HCO_3^-$) upon hydrolysis in a concentration of 0.1 M to 2.0 M and a reducing agent.
12. The reagent composition according to 11, characterized in that the reducing agent is selected from the group consisting of 2-Mercaptoethanol, 2-Mercaptoethylamine-HCl, TCEP, Cystein-HCl, Dithiothreitol (DTT), N-Methylmaleimide, Ellman's Reagent and 1,2-dithiolane-3-carboxylic acid.
13. The reagent composition according to 11, characterized in that the reducing agent is selected from the group consisting of 2-Mercaptoethanol, 2-Mercaptoethylamine-HCl, TCEP, Cystein-HCl and Dithiothreitol (DTT).

14. The reagent composition according to any one of 11 to 13, characterized in that the reducing agent has a concentration of 2 mM to 30 mM.
15. A reagent mixture comprising a sample to be investigated, a reagent composition according to any of 11 to 14, and an alkalinising agent.
16. The reagent mixture according to 15, characterized in that the alkalinising agent is selected from the group consisting of NaOH, KOH, Ca(OH)$_2$ and LiOH.
17. Use of a reagent composition according to any of 11 to 14 together with an alkalinising agent to release a vitamin D compound from vitamin D-binding protein.
18. A kit for the release of a vitamin D compound from vitamin D-binding protein, which contains a reagent composition according to any of the 11 to 14.
19. A kit for the detection of a vitamin D compound from vitamin D-binding protein, which contains a reagent composition according to any of the 11 to 14 and an alkalinising agent.

EXAMPLES

Example 1

Assays for the Detection of 25-Hydroxyvitamin D

Commercial assays are used according to the manufacturer's instructions. The 25-hydroxyvitamin D determinations are carried out by means of HPLC (test for 25(OH) vitamin D$_3$, from the "Immundiagnostik" Company, Bensheim, order No. KC 3400) or by means of LC-MS/MS (Vogeser, M. et al., Clin. Chem. 50 (2004) 1415-1417) as described in the literature.

The preparation of the ingredients and the general test procedure for a new test is described in the following:

1.1 Synthesis of hydroxyvitamin D2-3-2'-cyanoethyl ether 20.6 mg (50 μmol) 25-hydroxyvitamin D$_2$ (Fluka No. 17937) is dissolved in a 25 ml three necked round bottom flask with an internal thermometer in 10 ml dry acetonitrile under an argon atmosphere. 1.5 ml tert.-butanol/acetonitrile (9:1) is added to the solution and cooled to 6° C. in an ice bath. Subsequently 820 μl of an acrylonitrile solution (86 μl acrylonitrile in 1.0 ml acetonitrile) is added and stirred for 15 minutes at 6° C. Then 205 μl of a potassium hydride solution (25 mg KH in 0.5 ml tert.-butanol/acetonitrile 9:1) is added. A brief flocculation occurs after which a clear solution is obtained. The reaction solution is stirred for a further 45 minutes at 6° C. and subsequently for 60 minutes at 4° C.

Subsequently the reaction solution is diluted with 10 ml methyl-tert.-butyl ether and washed twice with 10 ml H$_2$O each time. The organic phase is dried with about 1 g anhydrous sodium sulfate, filtered over a G3 glass frit and evaporated on a rotary evaporator. It is dried in a high vacuum to form a viscous clear residue with a mass of about 55 mg.

1.2 Synthesis of hydroxyvitamin D$_2$-3-3-aminopropyl ether

The entire nitrile obtained above is dissolved in 15 ml diethyl ether and admixed with a suspension of 7.5 mg lithium hydride in 7.5 ml diethyl ether while stirring. The reaction mixture is stirred for 1 hour at room temperature. Afterwards a suspension of 38.4 lithium aluminium hydride in 6.6 ml diethyl ether is added. This results in a strong turbidity of the mixture. The reaction mixture is stirred for a further hour at room temperature, then the reaction mixture is cooled to 0-5° C. in an ice bath and 35 ml water is carefully added. The pH is made strongly basic by addition of 6.6 ml 10 M potassium hydroxide solution.

It is extracted three times with 65 ml methyl-tert.-butyl ether each time. The combined organic phases are dried using about 5 g anhydrous sodium sulfate, filtered and evaporated at room temperature on a rotary evaporator. The residue is dried to mass constancy using an oil pump. The crude product is dissolved in 5 ml DMSO and 3.0 ml acetonitrile and purified by means of preparative HPLC.

eluent A=Millipore-H$_2$O+0.1% trifluoroacetic acid;
eluent B=95% acetonitrile+5% Millipore-H$_2$O+0.1% TFA;
gradient: from 50% B to 100% B in 100 min
flow rate: 30 ml/min
temperature: room temperature
column dimension: Ø=5.0 cm; L=25 cm
column material: Vydac C18/300 Å/15-20 μm
det. wavelength: 226 nm Fractions whose product content is larger than 85% according to analytical HPLC (Vydac Cl 8/300 Å/5 μm; 4.6×250 mm) are pooled in a round bottom flask and lyophilized. 13.7 mg (yield: 58%) is obtained as a colourless lyophilisate.

1.3 Synthesis of hydroxyvitamin D$_2$-3-3'-N-(hemi-suberyl)aminopropyl-ether-biotin-(beta-Ala)-Glu-Glu-Lys(epsilon) conjugate (=Ag—Bi)

13.7 mg (25 μmol) hydroxyvitamin D$_2$-3-3'-aminopropyl ether is dissolved in 3.5 ml DMSO, 28.7 mg (30 μmol) biotin-(beta-Ala)-Glu-Glu-Lys(epison)-hemi-suberate-N-hydroxysuccinimide ester (Roche Applied Science, No. 11866656) and 12.5 μl triethylamine are added and it is stirred overnight at room temperature. The reaction solution is diluted with 4.5 ml DMSO, filtered through a 0.45 μm microfilter and subsequently purified by means of preparative HPLC (conditions see example 2.3 b)). Fractions that contain more than 85% product according to analytical HPLC are pooled and lyophilized. 9.8 (yield: 30%) purified biotin conjugate is obtained.

1.4 Ruthenylation of Vitamin D-Binding Protein and Purification by Gel Filtration Chromatography The vitamin D-binding protein is transferred to 100 mM potassium phosphate/150 mM sodium chloride buffer, pH 8.5 and the protein concentration is adjusted to 5-10 mg/ml. The ruthenylation reagent (ruthenium (II) tris (bipyridyl)-N-hydroxysuccinimide ester) is dissolved in DMSO and added to the antibody solution at a molar ratio of 3 to 1. After a reaction time of 45 min the reaction is stopped by addition of 1-lysine and the ruthenylated vitamin D-binding protein (=DBP-Ru) is purified by gel filtration on a Superdex 200 column.

1.5 Test Procedure in the Assay

The sample to be investigated is measured using the Elecsys® system from the Roche Diagnostics company.

The reagent mixture is formed by mixing a sample to be investigated with the reagent composition (A) and an alkalinising agent (B).

In this example the reagent mixture is formed of 15 µl sample mixed with 15 µl of the reagent composition (A) and 10 µl of the alkalinising agent (B). The reagent mixture is incubated for 9 minutes. In the next step 70 µl of detecting reagent (Solution C) is added to the reagent mixture and incubated for further 9 minutes. In the last step biotinylated wall antigen (Solution D) (60 µl) as well as 30 µl of magnetizable polystyrene particles coated with streptavidin (SA) (30 µl) (Suspension E) are added. After a further 9 minutes incubation the amount of bound ruthenylated vitamin D-binding protein is determined as usual (see FIG. 1, 2, 3, 4a, 4b).

Reagent composition (A) contains:

| | |
|---|---|
| 10 mM | NaOH |
| 4 mM | EDTA |
| 6.7 mM | dithiothreitol (DTT) |
| 0.5M | ethylene carbonate (EC) |
| pH 5.5 | |

Alkalinising agent (B) contains:
1.375 M NaOH

Solution C with the ruthenylated vitamin D-binding protein (DBP-Ru) contains:

| | |
|---|---|
| 0.2M | bis-tris-propane (pH 7.5) |
| 2.5% | human serum albumin (HSA) |
| 50 mM | NaCl |
| 1% | mannit |
| 0.1% | oxypyrion |
| 0.12 µg/mL | DBP-Ru |

Solution D with the biotinylated wall antigen contains:

| | |
|---|---|
| 0.2M | bis-tris-propane (pH 8.6) |
| 0.5% | tween-20 solution |
| 0.1% | oxypyrion |
| 30 ng/ml | biotin |
| 0.0108 µg/mL | Ag—Bi (from example 1.1) |

Suspension E with SA-coated latex particles contains:
0.72 mg/ml SA-coated magnetizable polystyrene particles having a binding capacity of 470 ng/ml.

Example 2

Comparison of Carbonate Ester to a Metal Salt, a Phosphate Buffer and a Carbonate The sample to be investigated is measured using the Elecsys® system from the Roche Diagnostics company. The total assay procedure is shown in example 1.5. In aberrance to example 1.5 the reagent composition (A) contains either 0.5 M ethylene carbonate (EC), 0.5 M $Na_2CO_3$, 0.5 M NaCl or 0.5 M $NaH_2PO_4$, respectively.

Reagent Composition (A):

| | |
|---|---|
| 10 mM | NaOH |
| 4 mM | EDTA |
| 6.7 mM | DTT |
| 0.5M | of either EC, $Na_2CO_3$, NaCl or $NaH_2PO_4$ |

Figure 5:
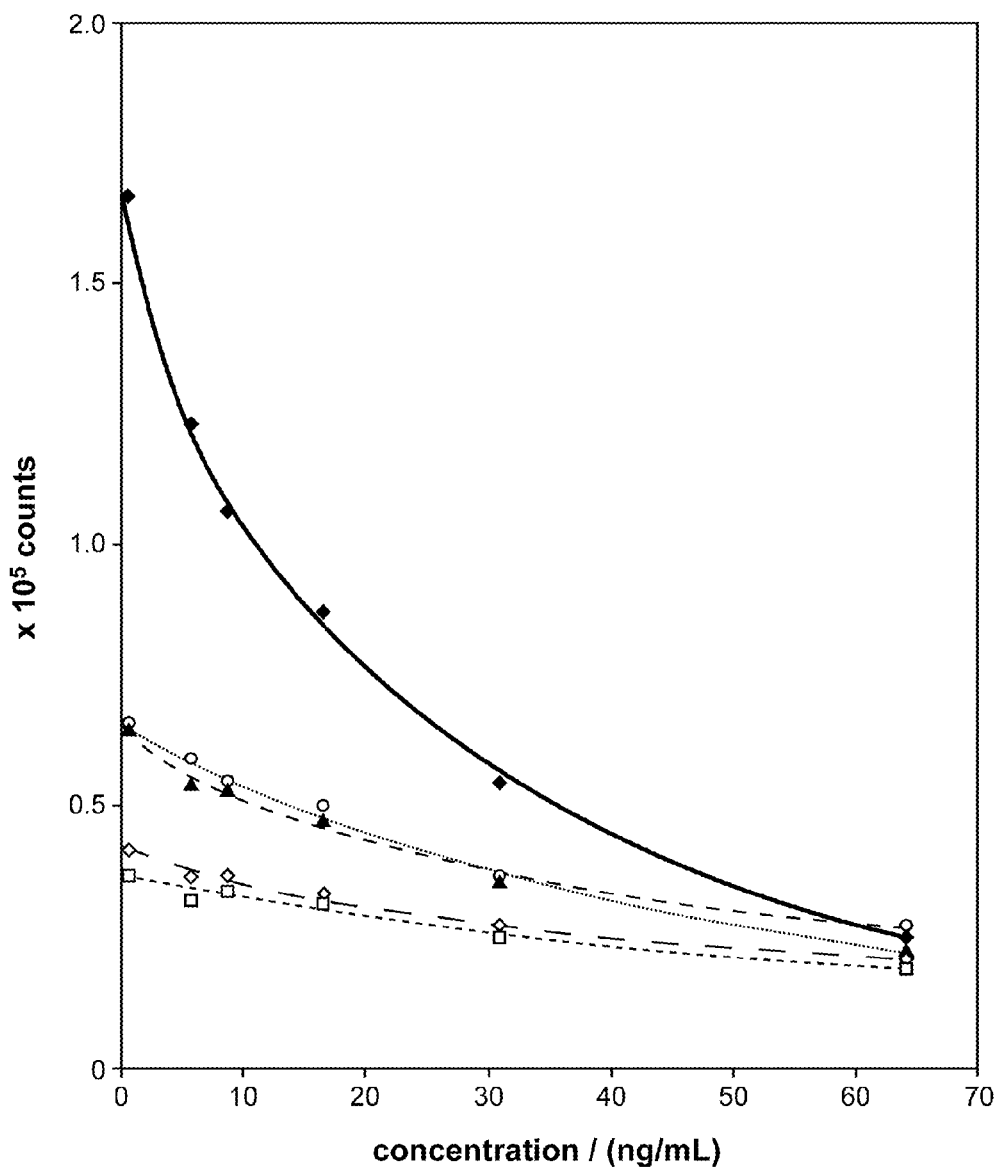
FIG. 5 Calibration curves of a Vitamin D assay as described in example 2 with reagent composition (A) containing 0.5 M ethylene carbonate (♦), 0.5 M $Na_2CO_3$ (○), 0.5 M $NaH_2PO_4$ (▲), 0.5 M NaCl (◇), and control (□). The X axis shows the concentration in ng/ml, the Y axis shows the counts determined as usual using the Elecsys® system from the Roche Diagnostics company.

As control a reagent composition (A) containing 10 mM NaOH, 4 mM EDTA, 6.7 mM DTT has been used. The results are shown in FIG. 5. The carbonate ester (0.5 M EC (◆) present in the alkaline pretreatment (reagent mixture) causes a signal enhancing effect in the competitive assay. Especially the signal dynamic is improved compared to a test without EC (□). A salt (0.5 M NaCl, (◇)) shows no effect. The addition of 0.5 M $Na_2CO_3$ (○) or 0.5 M $NaH_2PO_4$ (▲) shows a minor effect on the signal.

Example 3

Alkaline Pretreatment with/without Carbonate Ester

The sample to be investigated is measured using the Elecsys® system from the Roche Diagnostics company. The assay procedure is shown in example 1.5.

In aberrance to example 1.5 three different reagent compositions have been prepared containing either:
◆: 10 mM NaOH, 4 mM EDTA, 6.7 mM DTT, 0.5 M EC (see example 1.5)
or
▲: 10 mM NaOH, 4 mM EDTA, 6.7 mM DTT or
□: 10 mM NaOH, 4 mM EDTA.

Figure 6:
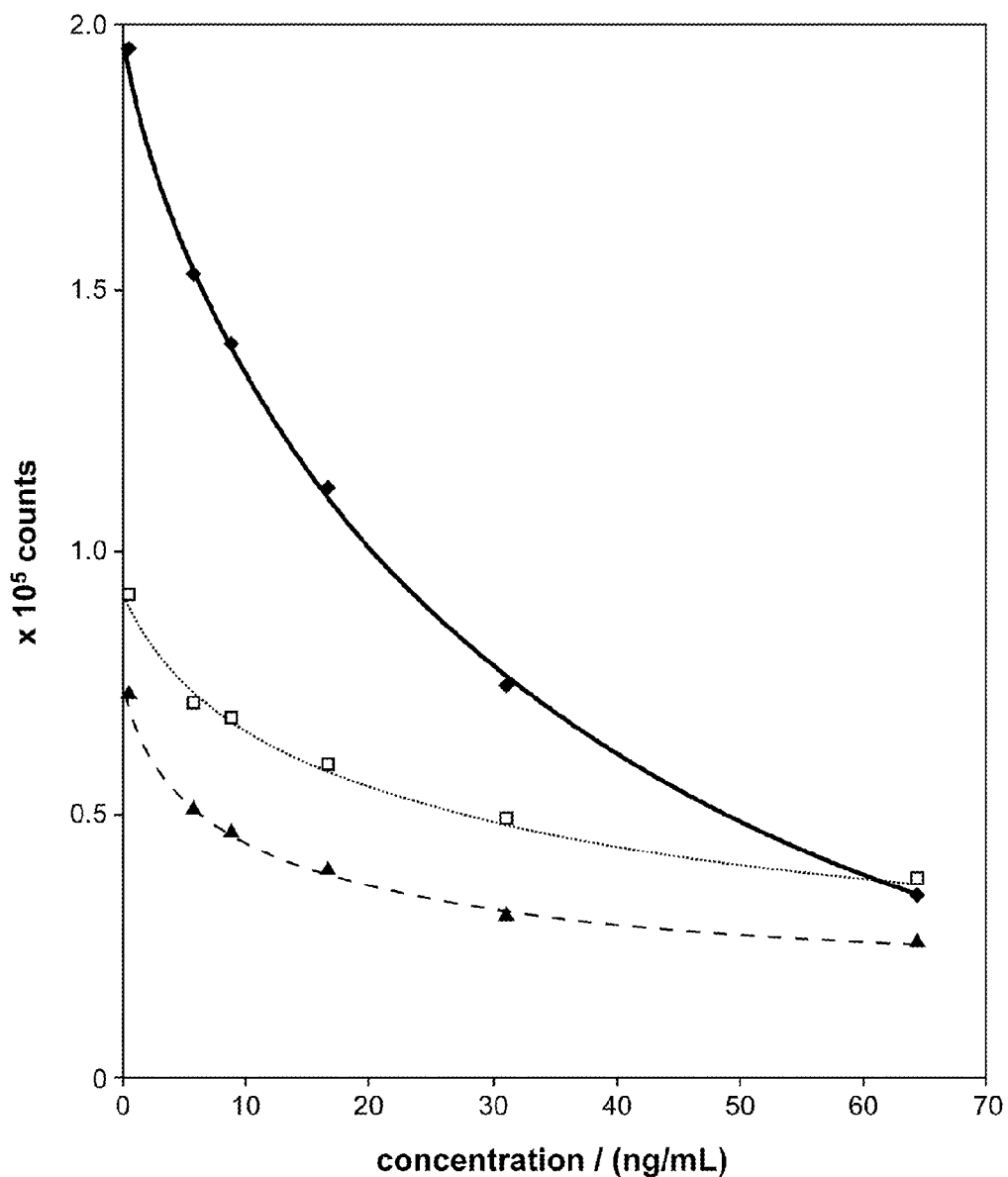
FIG. 6 Calibration curves of a Vitamin D assay as described in example 3 with reagent composition (A) containing: ♦: 10 mM NaOH, 4 mM EDTA, 6.7 mM DTT, 0.5 M EC, or ▲: 10 mM NaOH, 4 mM EDTA, 6.7 mM DTT, or □: 10 mM NaOH, 4 mM EDTA. The X axis shows the concentration in ng/ml, the Y axis shows the counts determined as usual using the Elecsys® system from the Roche Diagnostics company.

After a 4 min pretreatment incubation of sample+either ◆ (reagent composition (A)+alkalinising agent (B) as described in example 1.5), ▲, or □, respectively, (=reagent mixture) and before addition of solution C the pH of the reagent mixture has been set to pH 9 by addition of bis-tris-propane pH 6.3 (FIG. 6). The carbonate ester EC present in the alkaline pretreatment (reagent mixture) causes a signal enhancing effect in the competitive assay. Especially the signal dynamic is improved compared to a test without EC.

Example 4

Ethylene Carbonate Vs Dimethyl Carbonate

The sample to be investigated is measured using the Elecsys® system from the Roche Diagnostics company. The assay procedure is shown in example 1.5.

In aberrance to example 1.5 two different reagent compositions (A) have been prepared containing either:
○: 10 mM NaOH, 4 mM EDTA, 6.7 mM DTT, 0.5 M EC (see example 1.5)
or
◆: 10 mM NaOH, 4 mM EDTA, 6.7 mM DTT, 0.5 M dimethyl carbonate.

Figure 7:
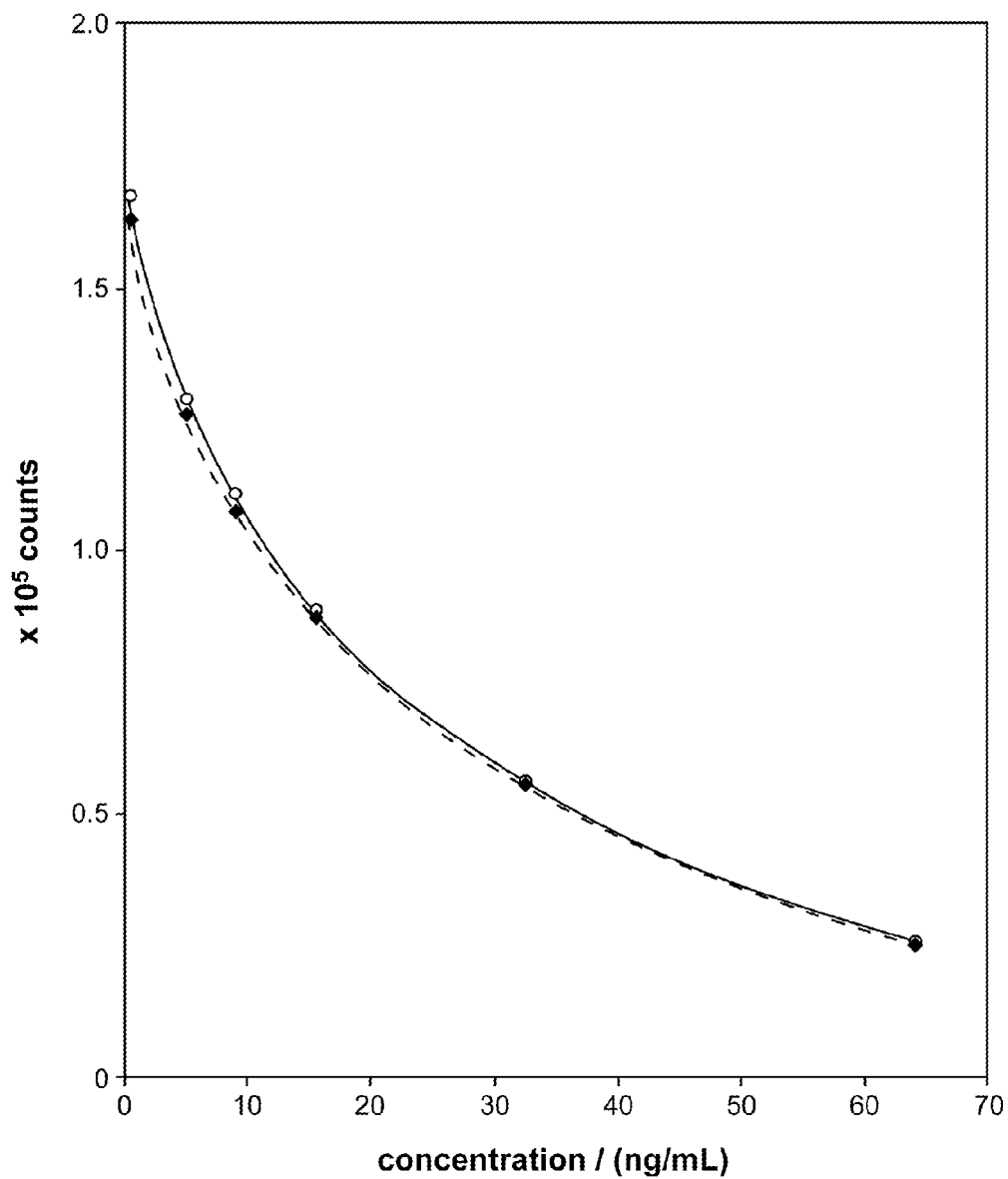
FIG. 7 Calibration curves of a Vitamin D assay as described in example 4 with reagent composition (A) containing: ○: 10 mM NaOH, 4 mM EDTA, 6.7 mM DTT, 0.5 M EC (see example 1.5), or ♦: 10 mM NaOH, 4 mM EDTA, 6.7 mM DTT, 0.5 M dimethyl carbonate. The X axis shows the concentration in ng/ml, the Y axis shows the counts determined as usual using the Elecsys® system from the Roche Diagnostics company.

Both carbonate ester, ethylene carbonate or dimethyl carbonate, respectively, show the same assay performance (FIG. 7).

Example 5

Effect of the Hydrolysis Products of Ethylene Carbonate

The sample to be investigated is measured using the Elecsys® system from the Roche Diagnostics company. The assay procedure is shown in example 1.5.

In aberrance to example 1.5 five different reagent compositions (A) have been prepared containing either:
◆: 10 mM NaOH, 4 mM EDTA, 6.7 mM DTT, 0.5 M EC (see example 1.5)
or
○: 10 mM NaOH, 4 mM EDTA, 6.7 mM DTT, 0.5 M $NaHCO_3$ or ▲: 10 mM NaOH, 4 mM EDTA, 6.7 mM DTT, 0.5 M NaHCO$_3$+0.5 M ethylene glycol ☐: 10 mM NaOH, 4 mM EDTA, 6.7 mM DTT.

Figure 8:
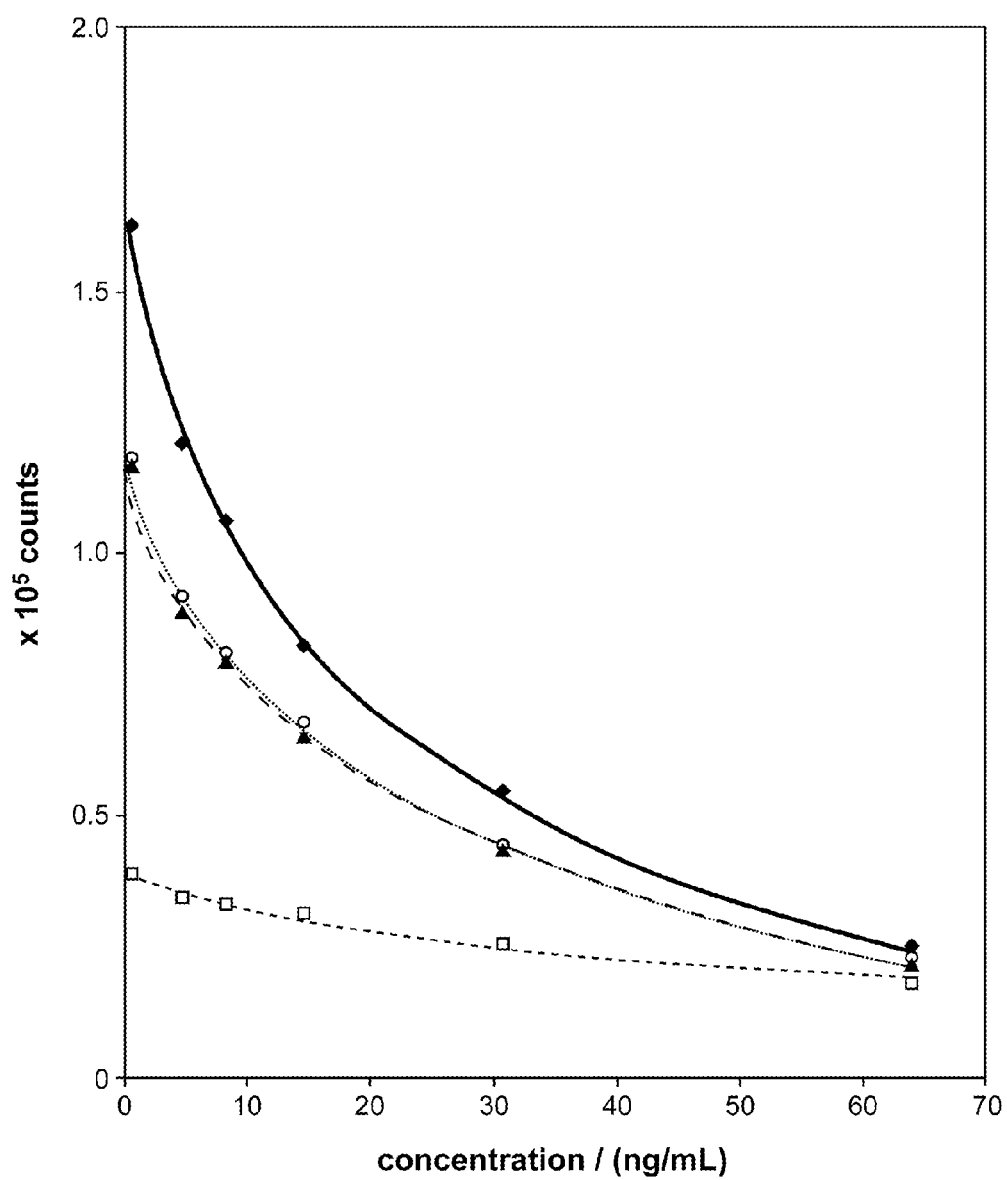
FIG. 8 Calibration curves of a Vitamin D assay as described in example 5 with reagent composition (A) containing: ♦: 10 mM NaOH, 4 mM EDTA, 6.7 mM DTT, 0.5 M EC (see example 1.5), or ○: 10 mM NaOH, 4 mM EDTA, 6.7 mM DTT, 0.5 M $NaHCO_3$, or ▲: 10 mM NaOH, 4 mM EDTA, 6.7 mM DTT, 0.5 M $NaHCO_3$+0.5 M ethylene glycol, or □: 10 mM NaOH, 4 mM EDTA, 6.7 mM DTT. The X axis shows the concentration in ng/ml, the Y axis shows the counts determined as usual using the Elecsys® system from the Roche Diagnostics company.

The alkaline hydrolysis product of EC is ethylene glycol, which has no influence on the assay (▲). A hydrogene carbonate salt (NaHCO$_3$) shows also a signal enhancing effect, but not as much as a carbonate ester (FIG. 8).

Example 6

Ethylene Carbonate Vs Glycerol 1,2 Carbonate

The sample to be investigated is measured using the Elecsys® system from the Roche Diagnostics Company. The assay procedure is shown in example 1.5.

In aberrance to example 1.5 two different reagent compositions (A) have been prepared containing either:
- ◆: 10 mM NaOH, 4 mM EDTA, 6.7 mM DTT, 0.5 M EC (see example 1.5)

or
- ○: 10 mM NaOH, 4 mM EDTA, 6.7 mM DTT, 0.5 M glycerol 1,2 carbonate.

Figure 9:
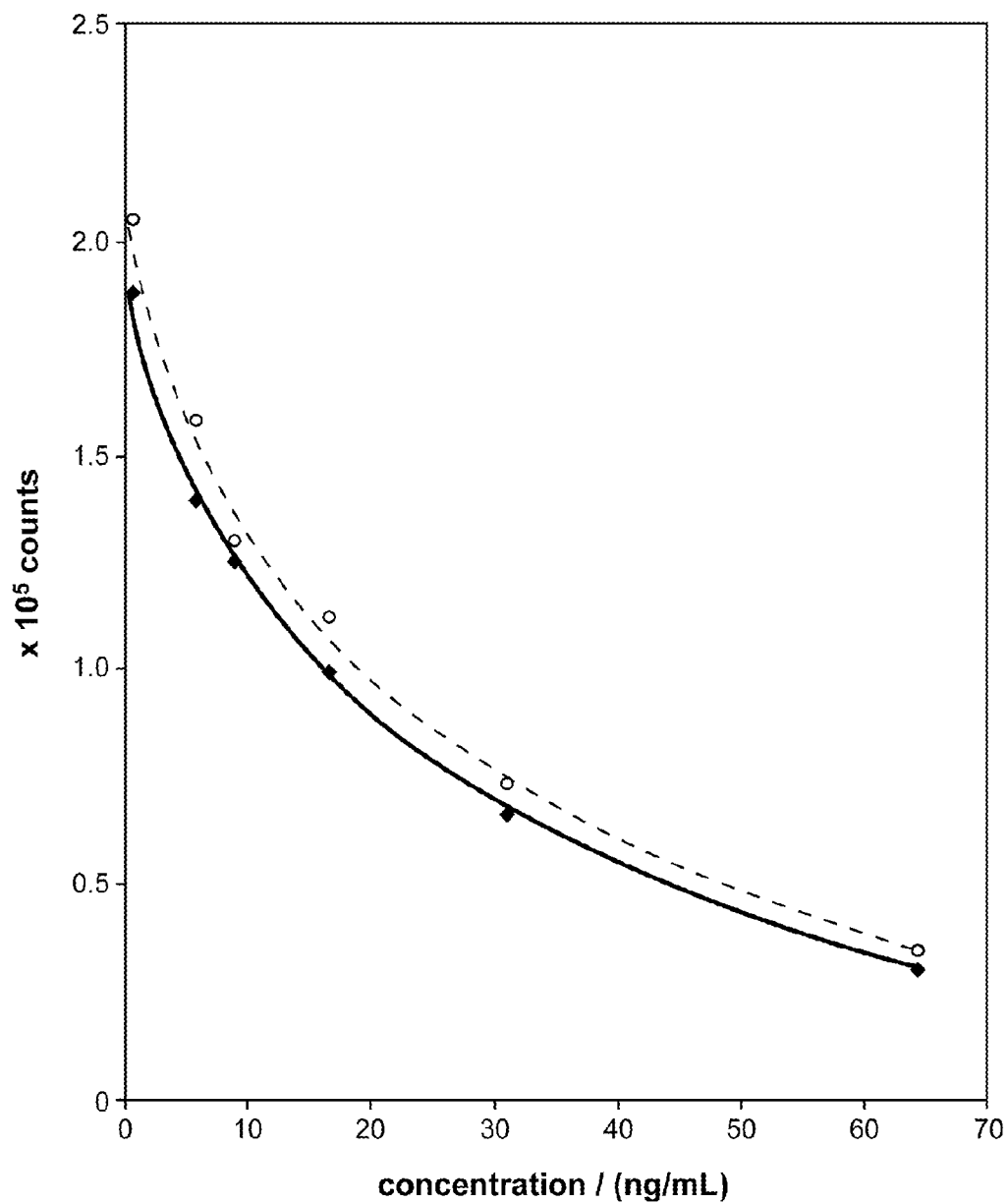
FIG. 9 Calibration curves of a Vitamin D assay as described in example 4 with reagent composition (A) containing: ♦: 10 mM NaOH, 4 mM EDTA, 6.7 mM DTT, 0.5 M EC (see example 1.5) or ○: 10 mM NaOH, 4 mM EDTA, 6.7 mM DTT, 0.5 M glycerol 1,2 carbonate. The X axis shows the concentration in ng/ml, the Y axis shows the counts determined as usual using the Elecsys® system from the Roche Diagnostics company.

Both carbonate ester, ethylene carbonate or glycerol 1,2 carbonate, respectively, show the same assay performance (FIG. 9).

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An in vitro method for releasing a vitamin D compound from a vitamin D-binding protein comprising the steps of:
   a) providing a sample that contains vitamin D and vitamin D-binding protein to be investigated; and
   b) mixing the sample from step (a) with:
      i) one of:
         a. a reagent containing a hydrogen carbonate salt in a concentration of 0.1 M to 2.0 M or
         b. a concentration of 0.1 M to 2.0 M of a substance that releases hydrogen carbonate ions (HCO3−) upon hydrolysis, wherein the substance that releases hydrogen carbonate ions (HCO3−) is selected from the group consisting of carbonate esters and pyrocarbonates; and wherein upon mixing, the substance is hydrolyzed, thereby releasing hydrogen carbonate ions;
      ii) a reducing agent, and
      iii) an alkalinising agent,
   thereby releasing the vitamin D compound from the vitamin D-binding protein of the sample from step (a).

2. The method according to claim 1, wherein the reagent according to step i) is soluble in an aqueous solution under the appropriate conditions for releasing a vitamin D compound from the vitamin D-binding protein.

3. The method according to claim 1, wherein the reagent according to step i) contains a hydrogen carbonate salt in a concentration of 0.1 M to 2.0 M.

4. The method according to claim 1, wherein the reagent according to step i) contains a substance capable of releasing hydrogen carbonate ions (HCO3−) upon hydrolysis in a concentration of 0.1 M to 2.0 M.

5. The method according to claim 1, wherein the substance that releases hydrogen carbonate ions (HCO3−) upon hydrolysis is a cylic or non-cyclic carbonate ester or a hydroxylated or halogenized derivative thereof, respectively.

6. The method according to claim 1, wherein the sample is a liquid sample.

7. The method according to claim 6, wherein the sample is blood, serum or plasma.

8. An in vitro method for measuring a vitamin D compound comprising the steps of:
   a) releasing a vitamin D compound from vitamin D-binding protein according to the method of claim 1 and
   b) measuring the vitamin D compound released in step (a).

9. The method according to claim 8, wherein the vitamin D compound is selected from the group consisting of 25-hydroxyvitamin D2, 25-hydroxyvitamin D3, 24,25-dihydroxyvitamin D2, 24,25-dihydroxyvitamin D3 and C3-epi 25-hydroxyvitamin D.

10. The method according to claim 9, wherein at least one of the vitamin D compounds 25-hydroxyvitamin D2 and 25-hydroxyvitamin D3 are determined.

11. A reagent composition for the release of a vitamin D compound from the vitamin D-binding protein comprising a reducing agent selected from the group consisting of 2-mercaptoethanol, 2-mercaptoethylamine-HCI, TCEP, Cystein-HCI, dithiothreitol (DTT), N-Methylmaleimide, Ellman's reagent and 1,2-dithiolane-3-carboxylic acid; an alkalizing agent selected from the group consisting of NaOH, KOH, Ca(OH)$_2$ and LiOH; and one of a hydrogen carbonate salt in a concentration of 0.1 M to 2.0 M or a concentration of 0.1 M to 2.0 M of a substance that releases hydrogen carbonate ions (HCO$_3^-$) upon hydrolysis, the substance selected from the group consisting of ethylene carbonate, dimethyl carbonate, glycerol 1,2-carbonate and propylene carbonate.

12. The reagent composition according to claim 11, characterized in that the reducing agent is selected from the group consisting of 2-Mercaptoethanol, 2-Mercaptoethylamine-HC1, TCEP, Cystein-HC1 and Dithiothreitol (DTT).

13. The reagent composition according to claim 11, characterized in that the reducing agent has a concentration of 2 mM to 30 mM.

14. A reagent mixture comprising:
   a sample to be investigated; and
   the reagent composition according to claim 11.

15. A kit for detecting the release of a vitamin D compound from a vitamin D-binding protein, comprising:
   a reagent composition according to claim 11; and
   an alkalinising agent.

* * * * *